US008061371B2

(12) United States Patent  (10) Patent No.: US 8,061,371 B2
Ochs et al.  (45) Date of Patent: Nov. 22, 2011

(54) MULTI-RIBBED DENTAL TAPE

(75) Inventors: Harold D. Ochs, Flemington, NJ (US);
Josef V. Knutzen, Yardley, PA (US);
Richard J. Fougere, Washington Crossing, PA (US); Alexander Lebovsky, Westfield, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 645 days.

(21) Appl. No.: 12/184,067

(22) Filed: Jul. 31, 2008

(65) Prior Publication Data

US 2009/0120454 A1  May 14, 2009

Related U.S. Application Data

(63) Continuation-in-part of application No. 11/937,025, filed on Nov. 8, 2007.

(51) Int. Cl.
*A61C 15/00* (2006.01)
(52) U.S. Cl. ......................................................... 132/329
(58) Field of Classification Search .................. 132/329, 132/325; 242/169, 159, 178
See application file for complete search history.

(56) References Cited

U.S. PATENT DOCUMENTS

| 4,450,849 | A | * | 5/1984 | Cerceo et al. ................. 132/321 |
| 4,646,766 | A | | 3/1987 | Stallard |
| 4,776,358 | A | | 10/1988 | Lorch |
| 4,836,226 | A | | 6/1989 | Wolak |
| 4,941,487 | A | | 7/1990 | VanBeneden |
| 4,996,056 | A | | 2/1991 | Blass |
| 4,998,978 | A | | 3/1991 | Varum |
| 5,209,251 | A | | 5/1993 | Curtis et al. |
| 5,226,435 | A | | 7/1993 | Suhonen et al. |
| 5,293,886 | A | | 3/1994 | Czapor |
| 5,357,989 | A | | 10/1994 | Gathani |
| 5,357,990 | A | | 10/1994 | Suhonen et al. |
| 5,413,127 | A | | 5/1995 | Hill |
| 5,518,012 | A | | 5/1996 | Dolan et al. |
| 5,588,452 | A | | 12/1996 | Peck |
| 5,657,779 | A | | 8/1997 | Blass et al. |
| 5,806,539 | A | | 9/1998 | Blass et al. |
| 5,865,197 | A | | 2/1999 | Bible et al. |
| 5,875,797 | A | | 3/1999 | Chiang et al. |
| 5,908,039 | A | | 6/1999 | Ochs et al. |

(Continued)

FOREIGN PATENT DOCUMENTS

EP  0832615 A  4/1998

(Continued)

OTHER PUBLICATIONS

Moore et al, "In vitro tooth whitening effect of two medicated chewing gums compared to a whitening gum and saliva", *BMC Oral Health* 2008, 8:23.

(Continued)

*Primary Examiner* — Todd Manahan
*Assistant Examiner* — Brianne O'Neill

(57) ABSTRACT

The present invention includes monofilament dental tapes for removing plaque and/or food debris from interdental spaces of a mammal, which dental tapes have a core body with an aspect ratio of greater than about 5:1 and a first cleaning surface and a second cleaning surface opposite the first cleaning surface, where at least one of the first and second cleaning surfaces includes a plurality of ribs disposed along the length thereof, and where the ratio of the width of the dental tape to the thickness of the dental tape is from about 4:1 to about 25:1.

8 Claims, 17 Drawing Sheets

U.S. PATENT DOCUMENTS

| | | | |
|---|---|---|---|
| 5,967,154 | A | 10/1999 | Anderson |
| 6,003,525 | A | 12/1999 | Katz |
| 6,016,816 | A | 1/2000 | Ariagno |
| 6,029,678 | A | 2/2000 | Tsao et al. |
| 6,039,054 | A | 3/2000 | Park et al. |
| 6,251,410 | B1 | 6/2001 | Schiraldi et al. |
| 6,340,027 | B1 | 1/2002 | Hagne et al. |
| 6,371,133 | B1 | 4/2002 | Gant |
| 6,453,912 | B1 | 9/2002 | Antler |
| 6,527,996 | B2 | 3/2003 | Schiraldi et al. |
| 6,536,448 | B2 | 3/2003 | McDevitt et al. |
| 6,545,077 | B2 | 4/2003 | Hill et al. |
| 6,575,176 | B1 | 6/2003 | Hill et al. |
| 6,591,844 | B2 | 7/2003 | Barlow et al. |
| 6,604,534 | B2 | 8/2003 | Hill |
| 6,609,527 | B2 | 8/2003 | Brown |
| 6,742,528 | B2 | 6/2004 | Dave |
| 6,884,309 | B2 | 4/2005 | Schweigert |
| 6,907,889 | B2 | 6/2005 | Brown |
| 6,916,880 | B2 | 7/2005 | Hill et al. |
| 7,055,530 | B2 | 6/2006 | Husted |
| 7,093,316 | B2 | 8/2006 | Chen |
| 7,281,541 | B2 | 10/2007 | Lorch |
| 2002/0078973 | A1 | 6/2002 | Marwah et al. |
| 2002/0081550 | A1 | 6/2002 | Karazivan |
| 2002/0104548 | A1 | 8/2002 | Bhupendra |
| 2003/0041873 | A1 | 3/2003 | Contratto |
| 2003/0230319 | A1 | 12/2003 | Marcon et al. |
| 2004/0063833 | A1 | 4/2004 | Chen |
| 2005/0133654 | A1* | 6/2005 | Metzger ............... 242/422.5 |
| 2006/0016457 | A1 | 1/2006 | Hoffman, III |
| 2006/0112968 | A1 | 6/2006 | Brown et al. |
| 2006/0237028 | A1 | 10/2006 | Hamidy |
| 2006/0243297 | A1* | 11/2006 | Brown ...................... 132/321 |
| 2009/0120454 | A1 | 5/2009 | Ochs et al. |

FOREIGN PATENT DOCUMENTS

| | | |
|---|---|---|
| EP | 2057965 A | 5/2009 |
| WO | WO 98/06350 A | 2/1998 |
| WO | WO 02/15814 A | 2/2002 |

OTHER PUBLICATIONS

Yankell et al., "Laboratory Evaluations of Three Dentifrices with Polishing or Brushing", Journal of Clinical Dentistry, vol. 9, issue 3, pp. 61-63 (1998).

* cited by examiner

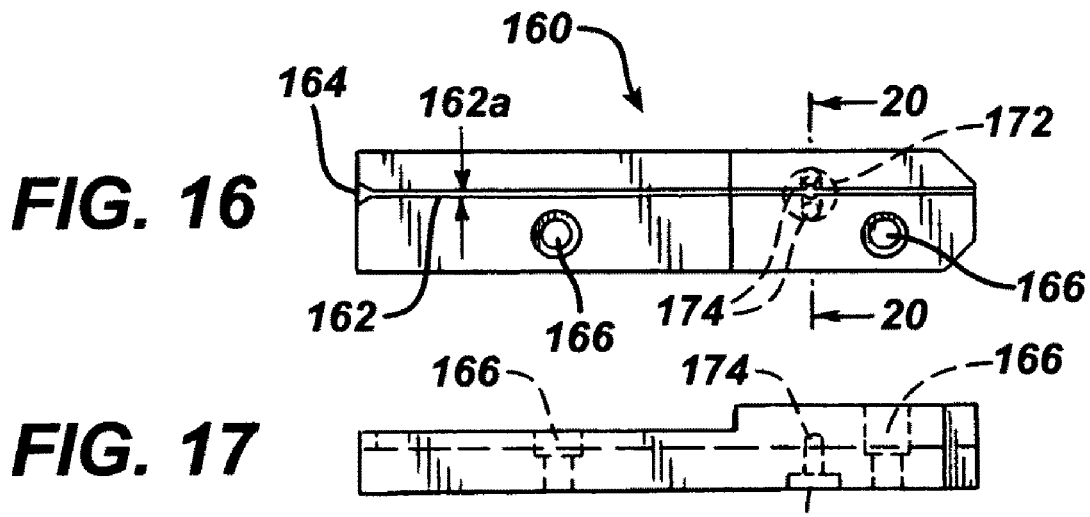
FIG. 16
FIG. 17
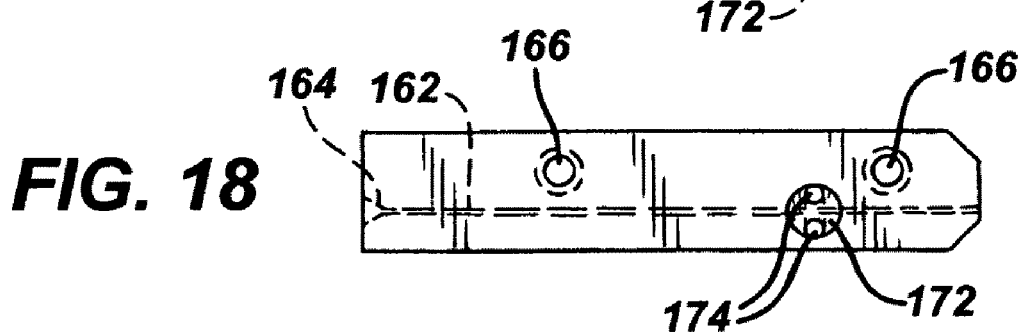
FIG. 18
FIG. 19
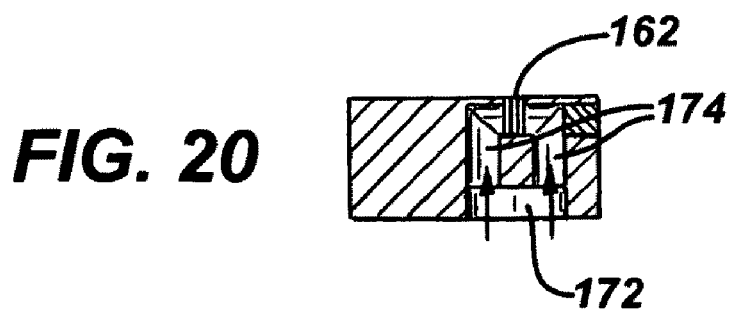
FIG. 20

MULTI-RIBBED DENTAL TAPE

This continuation-in-part application claims the benefit to U.S. patent application Ser. No. 11/937,025, filed Nov. 8, 2007, the entirety of which is hereby incorporated by reference as if fully set forth herein.

FIELD OF THE INVENTION

The present invention is directed to multi-ribbed dental tapes for the removal of food particles or debris and plaque from interstices between the teeth.

BACKGROUND OF THE INVENTION

Dental floss has been in use for more than 100 years for removing plaque and entrapped food particles from between teeth, as well as providing a clean feeling in the mouth. The original floss consisted of twisted silk placed in a jar. Since then, many improvements have been made to dental floss to make flossing more convenient and less problematic. Most improvements have been aimed at solving the negative aspects of flossing. These include reducing fraying and breakage, providing easier insertion between teeth and providing a softer, more gum and hand friendly floss. With the invention of nylon, a high tenacity fray-resistant yarn was used to replace the silk, providing more fray resistance. The addition of wax to twisted multifilament yarn helped anchor fibers together, while providing a lubricious coating for easier insertion. Similarly, the use of air-entangled fibers in combination with wax (see U.S. Pat. No. 5,908,039) provided a softer, more fray-resistant, and better cleaning multifilament floss. Low friction monofilament PTFE yarn coated with wax (see U.S. Pat. No. 5,518,012) provides good ease of insertion, depending upon the thickness and lack of twists or folds, as well as improved fray resistance. Unfortunately, PTFE monofilaments do not clean well, nor do they easily remove food particles from the space between teeth due to the low coefficient of friction of PTFE.

Improvement in the cleaning and particle removal characteristics was attempted by providing a pseudo monofilament product by encasing multifilaments in a soft polymer, (see U.S. Pat. Nos. 6,039,054 and 6,742,528). Such flosses slide easily between teeth, provide improved resistance to the PTFE products. Further improvements to flosses were attempted by providing monofilament tapes made of elastomeric materials which neck down when passing into the interdental space and then expand upon relieving tension. A low stretch variety is taught in U.S. Pat. No. 6,591,844. While this monofilament tape exhibits a higher elongation range than commercial floss, it is inferior in softness and mouth feel and fails to provide improved cleaning. A very soft "gel" floss is taught in U.S. Pat. No. 6,029,678, where the yarn is capable of being stretched to at least 200% of its original length, and as much as 2,000% of its original length. In tape form, this floss is at least 0.010 to 0.100-inch thick and more usually from 0.020 to 0.200-inch thick. This means that, while soft, the user will have to apply significant stretch to the product to make it pass between teeth. Once placed in the interdental cavity, this floss will expand and fill the interdental cavity. However, this floss has a smooth surface and is unlikely to remove much plaque or stuck food particles. With this degree of elongation, the consumer may find it difficult to maintain the necessary tension to move the floss up and down during the cleaning process.

Over the years, many improvements have been made to dental floss to make flossing more convenient and less problematic. However, each improvement is typically counterbalanced with a negative effect. Consumer-use tests and clinical studies have shown the monofilament flosses slide better with less fraying, while multifilament products clean better and remove more plaque, but are subject to fraying and breaking. The present invention provides a monofilament tape that not only cleans better than conventional monofilament flosses, but maintains the positive characteristics of monofilament flosses that make them desirable to consumers, such as mouth feel, easy slide between teeth and resistance to fraying or shredding.

SUMMARY OF THE INVENTION

The present invention is directed to monofilament dental tapes, preferably elastomeric monofilament dental tape, for removing plaque and/or food debris from interdental spaces of a mammal, which tapes include a core body having an aspect ratio of greater than about 5:1 and a first cleaning surface and a second cleaning surface opposite the first cleaning surface, where at least one of the first and second cleaning surfaces includes a plurality of ribs disposed along the length thereof, and where the ratio of the width of the dental tape to the thickness of the dental tape is from about 3:1 to about 25:1. In certain embodiments the core body of dental tapes of the present invention has an aspect ratio of greater than about 10:1 and at least about 8 ribs are disposed along the first and second cleaning surfaces.

BRIEF DESCRIPTION OF THE DRAWINGS

FIG. 16 is a top plan view of an entrance block of a coating die according to an exemplary embodiment of the present invention.

FIG. 17 is a right side elevational view of an entrance block of a coating die according to an exemplary embodiment of the present invention.

FIG. 18 is a bottom plan view of an entrance block of a coating die according to an exemplary embodiment of the present invention.

FIG. 19 is a front elevational view of an entrance block of a coating die according to an exemplary embodiment of the present invention.

FIG. 20 is a cross-sectional view of a entrance block pool and coating bores of a coating die according to the exemplary embodiment of FIG. 16 along the 20-20 plane.

FIG. 28$b$ is a front elevational view of a tape bobbin with tape wound around the bobbin spool core showing the bobbin spool core width relative to the bobbin tape width.

FIG. 29$b$ is a front elevational view of a tape bobbin movably positioned within a dispenser (phantom lined) depicting the relative bobbin spool core, bobbin tape and dispenser widths.

DETAILED DESCRIPTION OF THE INVENTION

The dental tapes of the present invention are in the form of a single monofilament. As used herein, the terms "tape", "yarn" and floss are interchangeable. The Monofilament dental tapes according to the present invention comprise a core body having first and second opposing cleaning surfaces, where at least one of the cleaning surfaces comprise a plurality of ribs disposed along the length thereof. As used herein, the term "rib" means a structural element integral with and protruding from the core body of the dental tape, which element has a configuration and dimension effective to provide for removal of plaque and/or food debris from interdental spaces of a mammal. Ribs may protrude substantially perpendicularly from the core body of the dental tape or at an angle. As used herein, the term "cleaning surface" means that surface of the dental tape that contacts the surface of the tooth when placed within the interdental space of the mammal, thereby providing for removal of plaque and/or food debris from the interdental space. The monofilament dental tape provides the tensile strength and base structure required for good dental floss properties. The dental tape can be made using commercially available material and known monofilament melt extrusion technology and equipment, it does not fray or break, is easy to hold, and readily accepts coatings.

Optionally, the dental tape is made using a material that provides a high degree of compressibility when extruded in the cross-sectional configurations of this invention, allowing it to slip through the tight spaces between teeth. Once in the cavity between teeth and into the interdental space, the dental tape substantially recovers from compression, providing cleaning surfaces containing ribs that act as scrapers to remove plaque and food particles from between the teeth.

Figure 1:
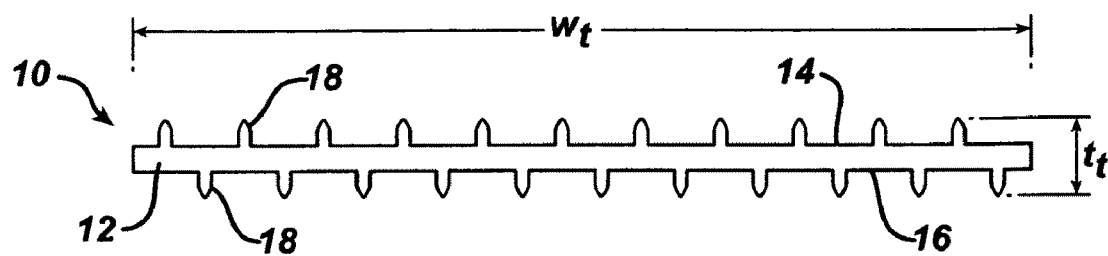
FIG. 1 is a cross-sectional view of one embodiment of the dental tape of the present invention.
Figure 2:
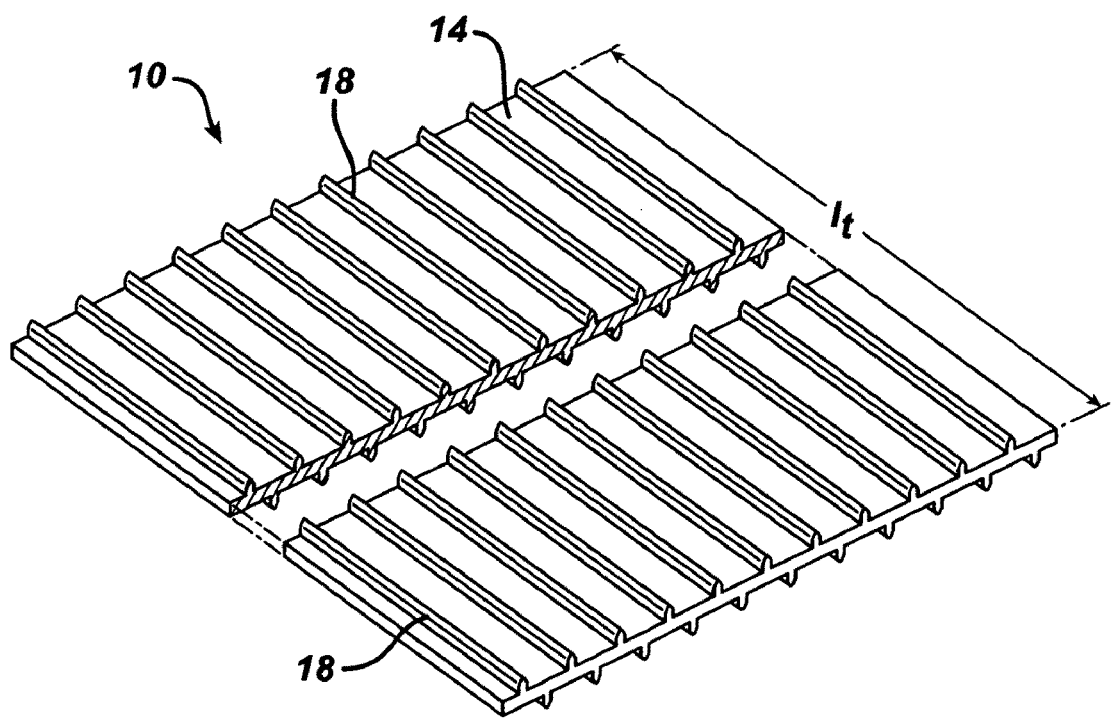
FIG. 2 is a perspective view of FIG. 1 looking from the top and front.
Figure 3:
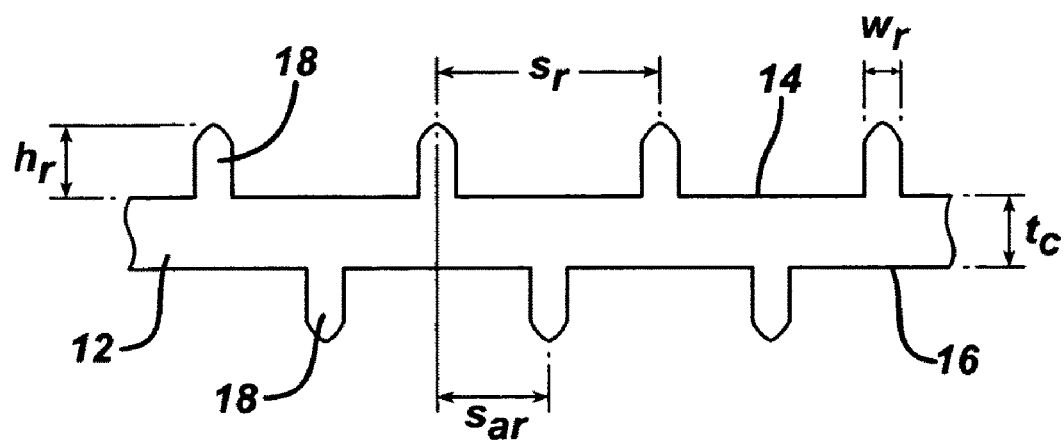
FIG. 3 is an enlarged cross-sectional view of the FIG. 1.

Turning to the drawings, exemplary monofilament dental tape 10 is illustrated in FIGS. 1-3. FIG. 1 shows a cross-sectional view of an embodiment of dental tape 10 comprised of core body 12 with first cleaning surface 14 and second cleaning surface 16. In the embodiment presented, ribs 18 protrude from both first cleaning surface 14 and second cleaning surface 16. In other embodiments, ribs may protrude from only one cleaning surface of the monofilament dental tape. The width of dental tape 10 is represented by $w_t$, while the thickness of dental tape 10 is represented by $t_t$.

The embodiment depicted in FIG. 1 shows a total of twenty-two ribs 18 protruding from cleaning surfaces 14 and 16 of monofilament dental tape 10, eleven from cleaning surface 14, and eleven from cleaning surface 16. In other embodiments of the present invention, the total number of ribs protruding from the cleaning surfaces of the dental tape may be greater than about eight, or greater than about twenty. FIG. 1 shows eleven ribs 18 protruding from both first and second cleaning surfaces 14,16 of monofilament dental tape 10. It is to be understood, however, that in other embodiments, the number of ribs protruding from the first cleaning surface of the dental tape may be the same, about the same, or significantly different than the number of ribs protruding from the second cleaning surface. In some embodiments, all ribs may be disposed along one of the first or second ribs. In addition, though the cross-sectional profile of the monofilament dental tape 10 shown in FIG. 1 is flat, it is to be understood that in other embodiments the dental tape can have other profiles, such as, but not limited to, arch, wave, or zig-zag.

FIG. 2 shows a perspective view of the FIG. 1 embodiment of dental tape 10 with first cleaning surface 14 and ribs 18 as seen from the top front. The length of dental tape 10 is represented by $l_t$.

FIG. 3 shows an enlarged cross-sectional view of the FIG. 1 embodiment of dental tape 10. The thickness of core 12 of dental tape 10 is represented by $t_c$. The height and width of ribs 18 are represented by $h_r$ and $w_r$, respectively. FIG. 3 shows an embodiment in which all ribs are uniform in height and width. It is to be understood that rib height and width can vary across the cleaning surfaces of the dental tape. For example, in one embodiment, ribs could be shorter and/or thinner at the edges of the cleaning surfaces than at the center of the cleaning surfaces.

The spacing between neighboring ribs 18 on first or second cleaning surface 14,16 of dental tape 10 is represented by $s_r$. In FIG. 3, $s_r$ is depicted as the spacing between neighboring ribs 18 on first cleaning surface 14 of dental tape 10. However, it is to be understood that $s_r$ could be used to measure the spacing between neighboring ribs 18 on either the first or second cleaning surfaces 14,16 of dental tape 10. FIG. 3 shows an embodiment in which the spacing ($s_r$) between neighboring ribs 18 on cleaning surfaces 14,16 of dental tape 10 are about equal for all ribs 18. However, it is to be understood that the spacing between neighboring ribs on either cleaning surface of the dental tape do not have to be about equal. So, for example, the spacing between the first two neighboring ribs could be represented as $s_{r1-2}$, while the spacing between the next two neighboring ribs could be represented as $s_{r2-3}$, etc. It is envisioned that in other alternative embodiments of the present invention, the spacing between some sets of neighboring ribs could be about equal, while the spacing between other sets of neighboring ribs are not about equal.

Figure 4:
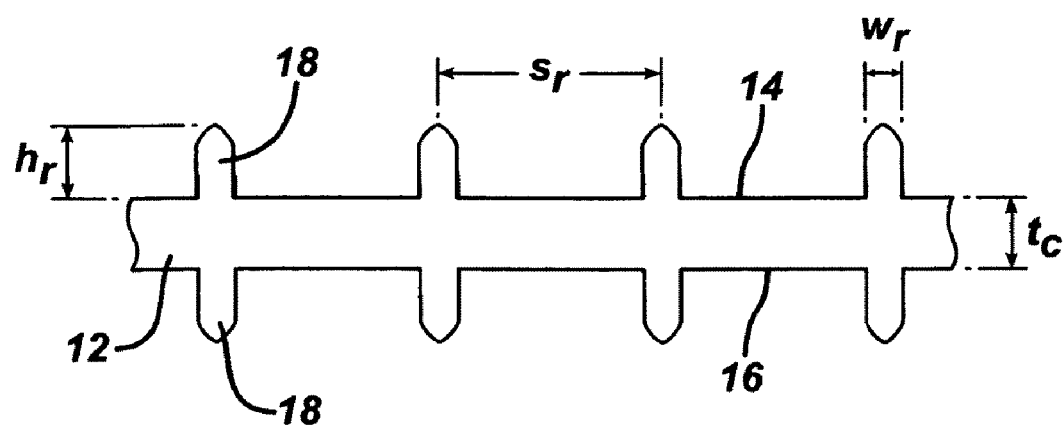
FIG. 4 is an enlarged cross-sectional view of another embodiment of the dental tape of the present invention.

The term $s_{ar}$ is used to show the spacing between alternating ribs, that is, the spacing between a rib 18 on first cleaning surface 14 and an adjacent rib 18 on second cleaning surface 16 of dental tape 10. FIG. 3 shows an embodiment in which spacing between alternating ribs $s_{ar}$ is about one-half the spacing between neighboring ribs $s_r$. So, the ribs on second cleaning surface 16 of dental tape 10 are offset such that they are positioned about midway between those on first cleaning surface 14. FIG. 4 shows an embodiment in which spacing between alternating ribs $s_{ar}$ is equal to the spacing between neighboring ribs $s_r$. So, the ribs on second cleaning surface 16 of dental tape 10 are aligned with those on first cleaning surface 14.

Figure 5A:
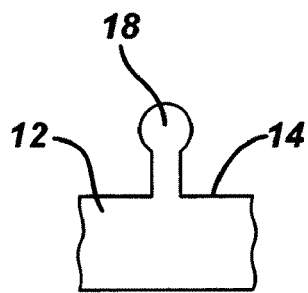
FIGS. 5a-5f are enlarged cross-sectional views of other embodiments of the ribs of the dental tape of the present invention.
Figure 5B:
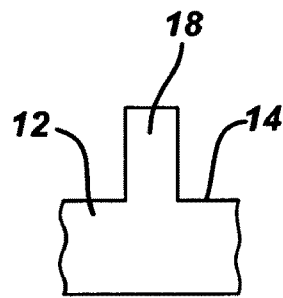
Figure 5C:
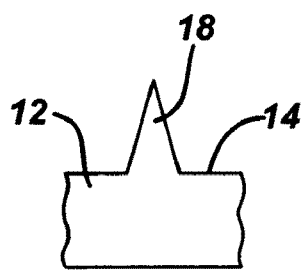
Figure 5D:
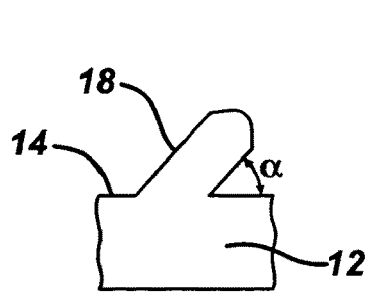
Figure 5E:
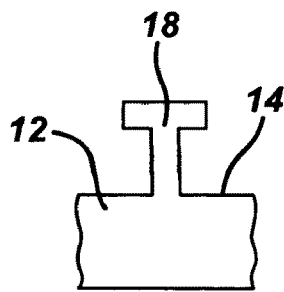
Figure 5F:
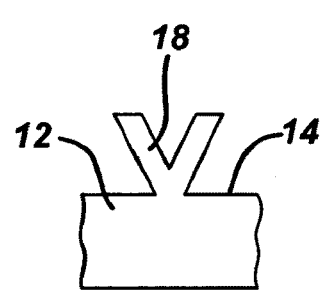

In the exemplary monofilament dental tape 10 embodiments illustrated in FIGS. 1-4, the cross-sectional shape of ribs 18 is shown as rectangular with a single rounded tip on the distal end of the rib. It is to be understood that other cross-sectional rib shapes are also contemplated embodiments of monofilament ribbed dental tape of the present invention. FIGS. 5a-5f show a number of other cross-sectional shapes of rib embodiments of the present invention. These rib shapes are just some of the shapes contemplated in the present invention, and it is to be understood that these shapes are not limiting to the spirit of the present invention. In FIG. 5a, the cross-sectional shape of rib 18 is shown as rectangular with a circular tip on the distal end of the rib. In other embodiments not shown, the tip on the distal end of the rib could be oval or semi-circular. FIGS. 5b and 5c depict ribs 18 with cross-sectional shapes that are rectangular and triangular, respectively. Rib 18 shown in FIG. 5d has a cross-sectional shape of similar to ribs 18 shown FIGS. 1-4, but rib 18 is shown protruding at an angle of alpha with respect to first cleaning surface 14 of dental tape 10. The cross-sectional shape of rib 18 shown in FIGS. 5e and 5f are approximately those of the English letters "T" and "V", respectively.

It is to be understood that all ribs on a given embodiment of the present invention may be, but are not required to be, of the same cross-sectional shape. A mixture of cross-sectional shapes may be employed as determined by the use of the ribbed monofilament dental tape.

Effective flossing of teeth involves placing dental floss into the interdental space between the teeth and then drawing the floss up against the side of each individual tooth to scrub as much of the tooth surface as possible. The monofilament ribbed dental tape of the present invention is inserted into the interdental space and moved thusly. Due to the configuration and dimensions of the ribs, the ribs act like squeegees to remove and trap/hold plaque and food debris in the spacing between the respective ribs with a higher degree of efficiency than, for example, a tape that does not include such ribs disposed along the length thereof, thus providing improved cleaning of the irregular surfaces of teeth.

The floss must be able to pass between tight teeth, a gap of several thousandths of an inch. It must be sized to fit through the gap, or be made of a material and construction that can compress when passing into the interdental space. The monofilament ribbed dental tape of the present invention is thin in one dimension to allow it to slide between tight teeth. It is wide in the other direction to provide two substantial cleaning surfaces to contact teeth surfaces. In certain embodiments the aspect ratio of the core body will be at least about 5:1, or at least about 10:1, or even at least about 35:1. The ratio of the width of the dental tape to the thickness of the dental tape may range from about 3:1 to about 25:1, or from about 10:1 to about 20:1.

The monofilament ribbed dental tape of the present invention can be made using a number of materials known in the art. These materials can be elastomeric or non-elastomeric. Some non-elastomeric materials from which the dental tape can be made include nylon or polytetrafluoroethylene (PTFE).

In certain embodiments, the dental tape is made of a material that can compress when passing into the interdental space, and then recover a percentage of its original form upon passing into the interdental space. Accordingly, dental tapes of the present invention provide a percent compression of greater than about 50 percent and a percent recovery of greater than about 40 percent, or in certain embodiments, a percent compression of greater than about 60 percent and a percent recovery of greater than about 60 percent. Also, since teeth surfaces are not regular, the interdental space between the teeth will be irregular, having areas which are more or less open, depending on the structure of the particular adjacent teeth. As such, in certain embodiments, the ribs are flexible relative to the core body such that they easily deflect to allow passage into the interdental space. In order to achieve optimal cleaning, it is desirable to have the ribs substantially recover their original dimensions once the force is removed and regain the majority of their original height once the dental tape is in the larger area of the interdental spacing. In this way, the rib will conform to the tooth cross sectional profile, removing more plaque and food.

In certain embodiments, the dental tape is made using an elastomeric material. Elastomeric materials provide a high degree of compressibility when extruded in the cross-sectional configurations of this invention, allowing it to slip through the tight spaces between teeth. Once in the cavity between teeth and into the interdental space, the dental tape substantially recovers from compression, providing cleaning surfaces that act as scrapers to remove plaque and food particles from between the teeth. Elastomeric materials that may be used to form the dental tape of the present invention include, but are not limited to polyamide-polyether block copolymers sold under the tradename PEBAX (Ato Chimie, Hauts-de-Seine France), such as PEBAX 7033, 5533 MX1205, 4033, 3533, and 2533; polyester-polyether block copolymers and polyester-polyester block copolymers sold under the tradename HYTREL (E. I. du Pont de Nemours & Co., Wilmington, Del.), such as HYTREL 7246, 5556, and 4056; aliphatic thermoplastic polyurethane elastomers sold under the tradename TECOFLEX (Lubrizol Advanced Materials, Inc., Cleveland Ohio); aromatic thermoplastic polyurethane elastomers sold under the tradename PELLETHANE (Dow Chemical Co., Midland, Mich.); and thermoplastic polyolefin elastomer sold under the name MULTI-FLEX (Dow Chemical Co., Midland, Mich.). A more detailed discussion regarding such elastomeric materials and their use in manufacturing dental tape can be found in U.S. Pat. No. 6,591,844 to Barlow et al. filed Aug. 23, 2001 and U.S. Pat.

No. 6,029,678 to Tsao et al. filed Jan. 21, 1998, both of which are herein incorporated by reference in their entirety.

Dimensions of the monofilament ribbed dental tape of the present invention may be as follows. The width of the dental tape, or $w_t$, is about 0.040 to about 0.100 inches, or about 0.070 to about 0.090 inches. The thickness of the dental tape, $t_t$, is about 0.0035 to about 0.012 inches, or about 0.007 to about 0.009 inches. The thickness of the core body of the dental tape, $t_c$, is about 0.001 to about 0.004 inches, or about 0.002 inches. The height of ribs 18, $h_r$, is about 0.0005 to about 0.004 inches, or about 0.002 inches. The width of the ribs, $w_r$, is about 0.0005 to about 0.003 inches, or about 0.0015 inches. The spacing between neighboring ribs on the cleaning surface of the dental tape, $s_r$, will depend on the width of the dental tape, and the number of ribs on the cleaning surface. For the monofilament ribbed dental tape of the present invention, spacing between neighboring ribs on a cleaning surface is about 0.003 to about 0.020 inches, or about 0.005 to about 0.010 inches.

The term $s_{ar}$ is used to show the spacing between alternating ribs, that is, the spacing between a rib on the first cleaning surface and a rib on the second cleaning surface of the dental tape. For the purposes of this disclosure, the ratio of $s_{ar}$ to $s_r$ defines the special relationship between alternating ribs. That ratio can vary from just greater than 0 when the ribs on the second cleaning surface are slightly out of alignment with those on the first cleaning surface, through 0.5 when the ribs on the second cleaning surface are positioned about midway between those on the first cleaning surface (see FIG. 3), to 1.0 when the ribs on the second cleaning surface are aligned with those on the first cleaning surface (see FIG. 4). In one embodiment of the monofilament ribbed dental tape of the present invention, the ratio of $s_{ar}$ to $s_r$ is about 0.5.

The monofilament ribbed dental tape of the present invention may be produced by commercial melt spinning process. In this process, the resin is fed into an extruder screw where the material is heated, melted and passed on to a melt pump. The melt pump meters the molten material into a die with a desired profile machined into the surface such that the profile is imparted on the molten extrudate as it exits the die. The extrudate passes from the die and is allowed to flow downwards and start the process of solidification. Some necking down is typical at that point. The material passes into a water bath where the solidification of polymer melt to solid tape is complete. The tape then undergoes a drawing process where it is stretched in the heated state and final characteristics are achieved. The final dental tape is wound onto spools. The spools can be placed on winding machines where the dental tape is wound into bobbins and the bobbins are placed into dispensers or, optionally, the spools are placed on coating machines first, where coatings can be applied prior to the winding operation.

Alternatively, the ribbed dental tape of the present invention may be comprised of multiple materials formed by co-extrusion, or lamination via rolling or adhesion processes.

Alternatively, the dental tape of the invention could also be produced from sheets of material. The resin would be extruded through a shaped die of the correct dimensions imparting the shape on the film. The extrudate passes from the die and is allowed to flow downwards and start the process of solidification. Some necking down is typical at this point. The material passes into a water bath where the solidification of polymer melt to solid tape is complete. The film could be slit at this point and drawn to final dimensions or it could be drawn first and then slit.

In certain embodiments of the monofilament ribbed dental tape of the present invention, coatings can be placed on the first or second cleaning surface of the dental tape. Coating compositions for use in the present invention must reliably adhere to the surface of the dental tape. The coating composition must have sufficient adherence to keep the coating on the surface of the dental tape during coating, winding, shipping and unwinding of the dental tape.

Suitable insoluble coatings include, but are not limited to, microcrystalline wax, beeswax, paraffin waxes, low molecular weight polyethylenes, silicone oils, essential oils, and mineral oil. Typically, the insoluble wax coatings have melting temperatures ranging from about 25° C. to about 100° C., optionally from about 35° C. to about 80° C. The waxes may be combined with water insoluble colorants that are FD&C approved for use in the mouth. Suitable colorants include, but are not limited to, synthetically derived colorants such as FD&C Blue #1 Lake, FD&C Blue #2 Lake, FD&C Red #40 Lake, Erythrosin Lake, Amaranth Lake, Ponceau 4R Lake, Carmoisosine Lake, Carmine Lake and colorants generated by converting a naturally derived dye to an aluminum or calcium based salt. Natural colorants such as titanium dioxide and the like may also be used.

The coating composition applied to the dental tape may be a soluble coating, i.e., the coating is such that it tends to dissolve or disperse in saliva present in the oral cavity. Such soluble coatings include soluble waxes or the like, which include, but are not limited to, low molecular weight polyethylene glycols ("PEGs"), such as PEG 1000 and PEG 1450. Combinations of higher molecular weight PEGs and lower molecular weight PEGs, such as a mixture of PEG 3350 and PEG 1000 may be used. Blends of liquid PEG's with high molecular weight PEG's may also be used.

Other coatings include meltable surfactants such as Polyoxamer 407; sialagogues; olfactory stimulants; sensates; essential oils; actives, such as fluoride; cetyl pyridinim chloride (CPC); tetra sodium pyrophosphate; whitening agents such as calcium peroxide, hydrogen peroxide, carbamide peroxide and other peroxide compounds capable of generating hydrogen peroxide in-situ; antimicrobials; anti-virals and mixtures thereof.

Such ingredients may be employed as solids, liquids, particles, gels, or the like, and may be encapsulated in conventional polymeric materials by conventional encapsulation techniques to form encapsulated materials having a polymeric shell and a core comprising the ingredient in one of the noted forms, as the case may be. Such ingredients also may be applied directly to the dental tapes of the present invention without the need for a coating carrier, where appropriate.

A coating comprising an insoluble wax may be applied, wherein the coating contains encapsulated components such as spray dried flavors, essential oils, or other ingredients protected and released from soluble spheres within the insoluble wax, or a soluble coating may be applied directly to the yarn or over the insoluble coating. The soluble coating may contain ingredients that are placed directly in the wax or through the use of spray dried or other encapsulation technologies commonly practiced within the art.

In certain embodiments, two insoluble coatings are applied to the dental tape. In these embodiments, the second coating composition must have a lower melting point than the first coating composition.

A soluble coating can be used by itself or as a second coating over an insoluble coating. One or both coatings can contain colorants, flavors, sweeteners, abrasives, anti-tartar agents, actives, such as fluoride salts, and like additives known in the art.

Additional components can be added to coatings for various benefits. These include flavor systems, such as spray dried flavors, flavor enhancers, and sweeteners, such as sodium saccharin. The amount of flavor added typically ranges from 10 percent to 25 percent, based on the total weight of the coating composition. The amount of sweetener typically ranges from 0.1 percent to 1 percent, based on the total weight is of the coating composition.

Other components can be added to coatings to assist in cleaning the teeth. These include actives including abrasives such as silica or di-calcium phosphate, and anti-tartar agents such as tetra-sodium-pyrophosphate. Where two coatings are used, actives are usually added in the second soluble coating to guarantee that a high percentage of the active will be released from the floss during use.

In formulating a coating, it is desirable to limit the amount of solid additives in the coating composition below about 30% by weight. Coating a dental tape with a coating composition having a solid additive content above this amount may cause difficulty in achieving uniformity of coating and reduce the ability of the coating to adhere to the tape surface. Coatings containing high amounts of solid additives may tend to flake off during processing and during use of the final product.

The dental tape coating may be anhydrous or hydrous. When the coating is hydrous, the water is evaporated upon drying.

The coating may be applied as an add-on typically ranging from about 10 percent to about 60 percent, optionally from about 20 percent to about 50 percent, based on the weight of the fiber substrate.

In certain embodiments, the dental tape is manufactured using equipment and processes capable of doing the following:

1. Feeding monofilament tapes made of elastomeric materials to a coating die at a controlled speed and tension so as to avoid telescoping issues,
2. Pumping the coating composition in a uniform fashion into the coating die,
3. Uniformly and simultaneously applying the coating composition to both sides of the dental tape, and
4. Providing a sufficient period of time during which the coating composition is substantially undisturbed on the dental tape until it is solidified intact.

Figure 7:
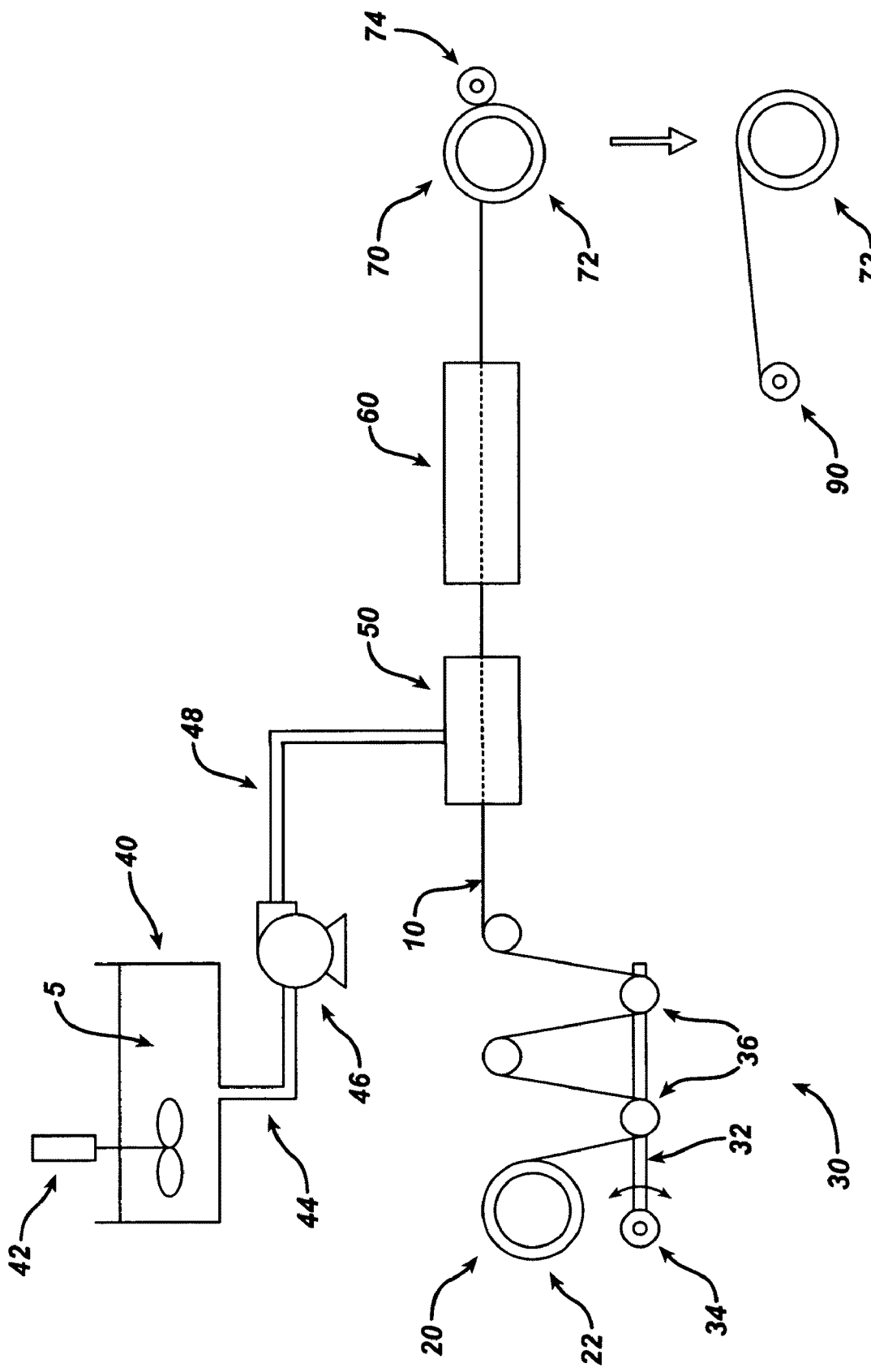
FIG. 7 is a schematic illustration of one embodiment of the manufacturing line for unwinding, coating and rewinding the dental tape of the present invention.

By "uniform" or "substantially uniform," it is meant that, when manually (without the aid of measuring instrumentation) or visually (without the need for magnifying devices beyond corrective eyewear) inspected, the coating should have an even (or relatively [or, substantially] even) thickness and be free from (or sufficiently [or substantially] free from) defects (such as pinholes or voids) in the coated area. The above-mentioned process for manufacturing the elastomeric monofilament dental tape of the invention is illustrated in FIG. 7. In the first step, the coating composition 5, typically a wax, is liquefied if necessary, as by heating, in a mix tank 40. A high sheer mixer 42, such as a Rotostat High Sheer Mixer Model #XPBL, made by Admix, can be used to keep coating composition 5 homogeneous. Typically, a Rotosolver head blade is used in the high sheer mixer 42 and is operated at, e.g., 1700 rpm.

The coating composition is then allowed to flow from mix tank 40, via a first pipe 44 into a positive displacement pump 46 which, when driven at a given speed, delivers a constant amount of coating, via a second pipe 48, to a coating die 50. The positive displacement pump can be a vane type positive displacement pumps, piston pumps, or similar type pumps. In certain embodiments, a Kerr piston pump, supplied by Kerr Corp., Sulfur, Ok., is used. Piston pumps, generally, facilitate the evenness and uniformity of coatings where the coating composition 5 contains solid particulates such as abrasives. In certain embodiments, positive displacement pumps are used since the passages bores, pipes, channels or outlets used in such embodiments to deliver coating composition 5 are generally positioned or oriented such that the directional path or track of the passage bores, pipes, channels or outlets points upwardly and toward or horizontally level with and toward the position of the dental tape 10 to be coated such that gravity has no effect or minimal effect on the flow of the coating composition from mix tank 40 onto the dental tape 10.

In certain embodiments, the dental tape 10 is simultaneously fed and pulled through the process by a combination of a powered unwinding system 20 and a floss rewinding system 70. The dental tape 10 is fed or unwound at a low tension and, in certain embodiments, pulled perpendicularly from feed spool 22 across or through sensing arm assembly 30. Sensing arm assembly 30 is provided for monitoring the tension of the dental tape 10 as it enters coating die 50. In certain embodiments, the sensing arm assembly 30 has an arm 32, a pivot point 34, and rollers 36 over which the dental tape 10 passes. Sensing arm assembly 30 is used to maintain a substantially constant low feeding or unwinding tension on dental tape 10 by adjusting the speed of power unwinding system 20 as it is simultaneously fed and pulled into the coating process system. In certain embodiments, where the dental tape passes through the coating process at line speed rates greater than about 1000 fpm, or optionally from about 1500 fpm to about 2500 fpm, or optionally from about 2000 fpm, the constant low unwinding tension is generally maintained at from about 50 grams-force to about 100 grams-force, optionally at from about 60 grams-force to about 100 grams-force for dental tape 10 having denier of about 400 to about 1200.

After coating, dental tape 10 is collected on a take-up spool 72. The speed at which take-up spool 72 operates is controlled by an electronic controller system. The controller may be a computer, a programmable logic controller or similar device. In the embodiment shown in FIG. 7, a speed sensing roll 74 rides on surface of the tape on take-up spool 72. Speed sensing roll 74 generates a signal which is fed to an electronic controller, such as a Fenner M-drive. The controller controls the voltage of motor 80 (shown in FIG. 8) which drives the speed of take-up spool 72. The use of the signal generated by speed sensing roll 74 in controlling the speed of take-up spool 72 helps to maintain a constant speed or velocity of the dental tape 10 through the coating process, controlling and maintaining the tension on dental tape 10 to less than 250 or (about 250) grams-force. The electronic controller also controls the speed of positive displacement pump 46. Thus the velocity of dental tape 10 is maintained while a constant amount of coating composition 5 is pumped into the coating die 50.

Figure 14:
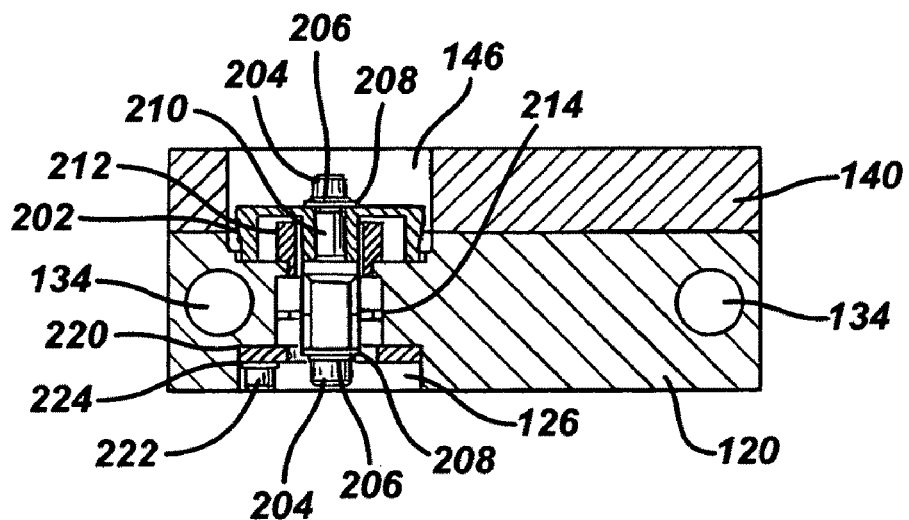
FIG. 14 is a cross-sectional view of a roller assembly of a coating die according to the exemplary embodiment of FIG. 12 along the 14-14 plane.

In certain embodiments, not shown in FIG. 7, the coating die 50 contains at least two rollers around which elastomeric dental tape 10 has at least some wrap. In certain embodiments, the number of rollers can range from 2, optionally 3, optionally 4 or greater rollers, or optionally 2 to 7 rollers or, optionally, from 3 to 5 rollers. Generally, dental tape 10 wraps around the rollers at from about 90° to about 270°. The rollers assist in applying coating composition 5 to dental tape 10. Downstream of the rollers there is typically a slot die region where coating composition 5 is smoothed onto the surface of dental tape 10. In certain embodiments, the slot die is in the form of a groove having parallel sides or walls, the groove, optionally, having a radius at its bottom for guiding the dental tape into a slot. In certain embodiments, the slot is sized such that excess coating is removed from dental tape 10 as it passes through the die (as shown at FIG. 14) while, at the same time, minimizing any additional tension on dental tape 10 caused by the slot die as the tape 10 passes through the die. As will be apparent to those skilled in the art, the dimensions of the groove and slot will depend upon such factors as the denier and type of elastomeric monofilament dental tape 10 and the amount of coating composition 5 being applied thereto.

In certain embodiments, a coating die useful in coating high surface area elastomeric dental tapes may be used. Such coating dies are adapted to receive or orientate the dental tape 10 such that the planar surface of the dental tape 10 is in a vertical position (or oriented such that the width dimension of dental tape 10 is perpendicular to horizontal plane of the coating die base) (as described in FIG. 11). Without being limited by theory, it is believed that such a vertical orientation better facilitates evenness and uniformity of the coating across the sides of the planar surface of the dental tape 10 than does movement of a horizontally oriented tape through the coating die.

Figure 9:
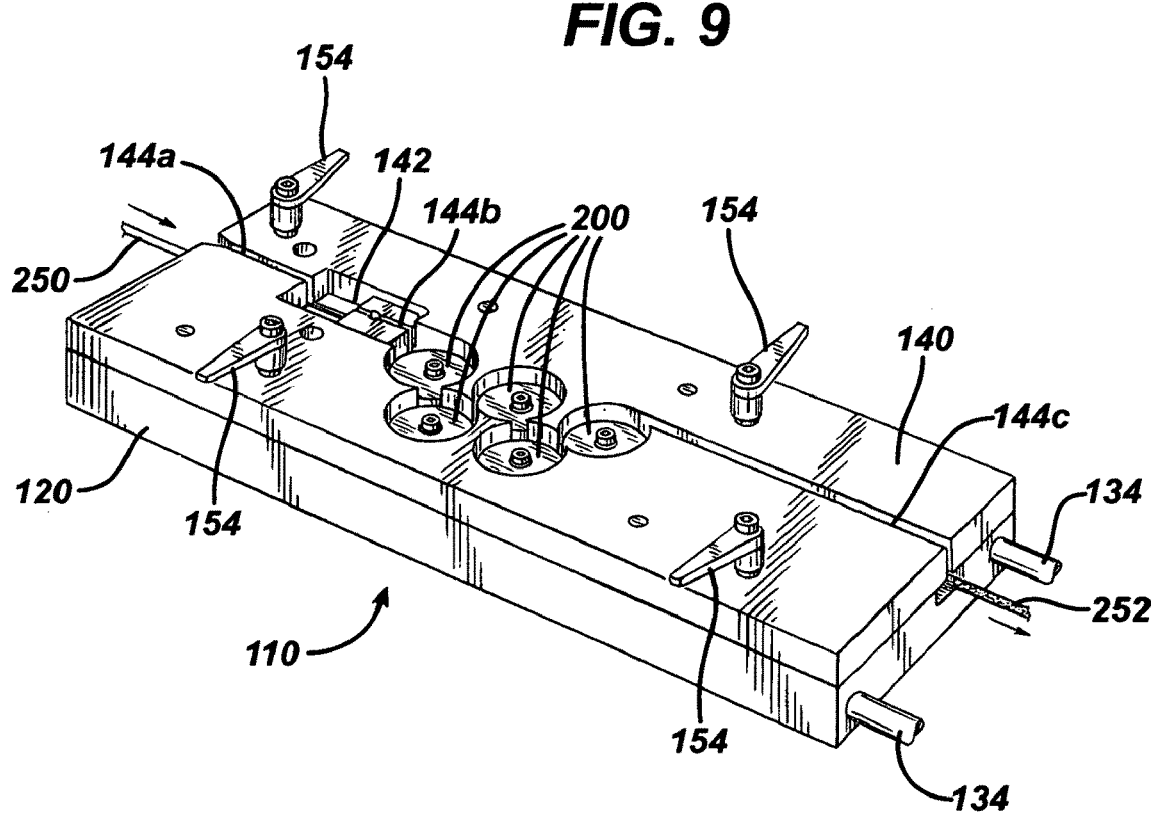
FIG. 9 is a perspective view of a roller coating die according to an exemplary embodiment of the present invention.

One embodiment of a coating die useful in coating high surface area elastomeric dental tapes is shown in FIGS. 9 to 24. FIG. 9 is a perspective view of roller coating die 110, including roller die base 120 and cover plate 140. Uncoated elastomeric dental tape 250 enters coating die 110 such that the planar surface of the dental tape 250 is vertically oriented or oriented such that its width dimension of dental tape 250 is perpendicular to roller die base 120. Dental tape 250 traverses vertically along cover plate die slot 144 and roller assemblies 200, and exits as vertically oriented, coated dental tape 252. FIG. 9 shows three sections of cover plate slot 144. Slot 144a traverses from the die entrance to entrance block window 142. Slot 144b traverses from entrance block window 142 to roller assemblies 200. Slot 144c traverses from roller assemblies 200 to the die exit.

Optionally, heaters can be incorporated into or associated with the coating dies of the present invention. The heaters are used to provide temperatures sufficient to keep the coating composition, typically a waxy material, flowable or in a liquid state. Such temperatures typically range from 180° F. to about 200° F. FIG. 9 shows an exemplary embodiment of the present invention having two cartridge heaters 134, which can be used for heating the rollers and/or other components of coating die 50.

Figure 10:
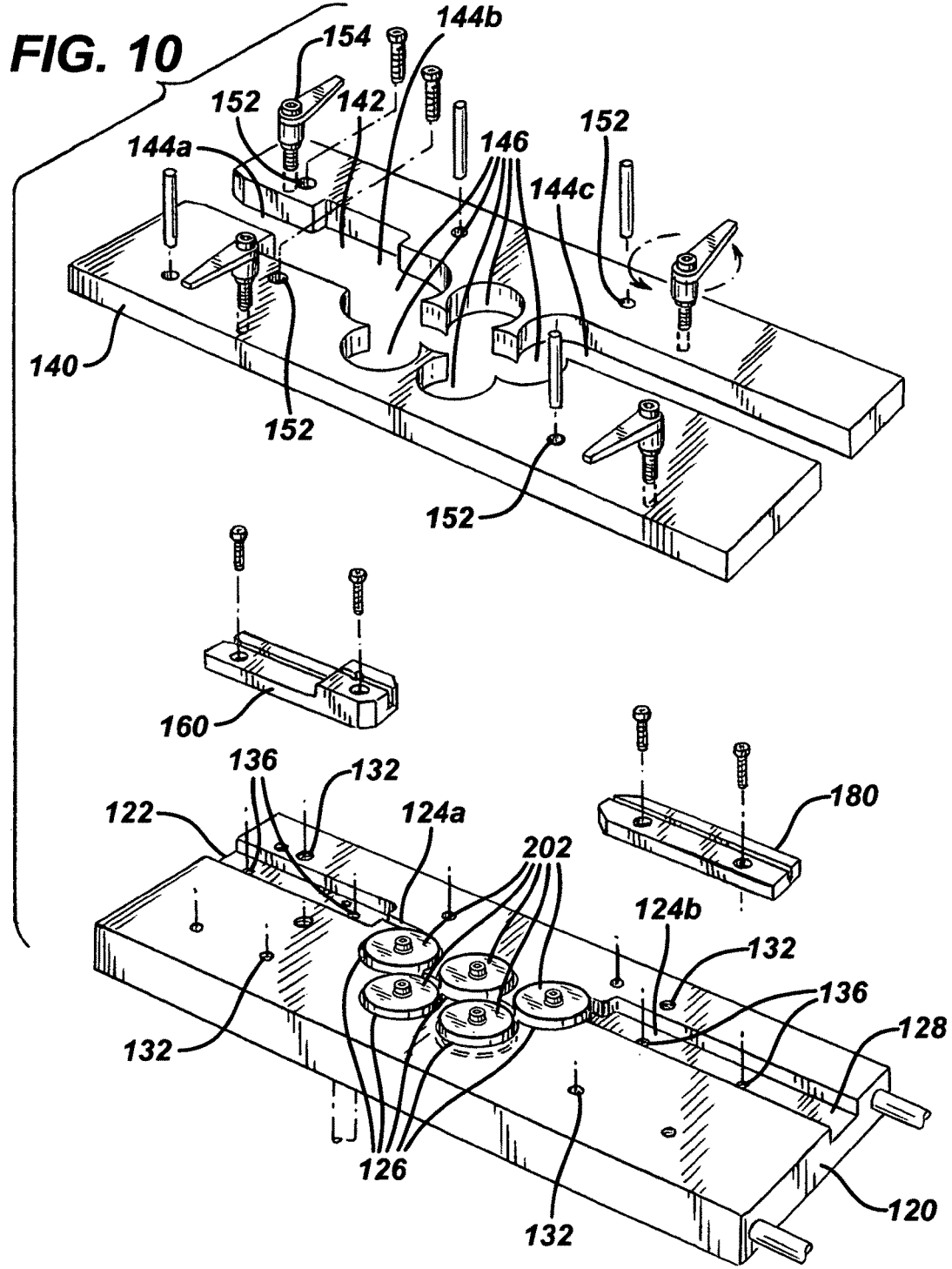
FIG. 10 is an exploded perspective view of a roller coating die according to an exemplary embodiment of the present invention.

FIG. 10 is an exploded perspective view of roller coating die 110, showing more details of roller die base 120 and cover plate 140. In addition to the three sections of cover plate slot 144 and cover plate window 142, five roller wheel windows 146, and four cover plate attachment holes 152 are shown on cover plate 140. Cover plate attachment holes 152 align with roller die base attachment holes 132. Roller die base attachment holes 132 are threaded. Threaded handle 154 is used to hold together roller die base 120 and cover plate 140.

Roller die base 120 includes entrance block recess 122, roller assembly recesses 126, exit block recess 128, roller die base attachment holes 132, and entrance and exit block attachment holes 136. FIG. 10 shows two sections of base slot 124. Base slot 124a traverses from entrance block recess 122 to roller assembly recesses 126. Slot 124b traverses from roller assembly recesses 126 to exit block recess 128. Entrance and exit block attachment holes 136 are threaded.

FIG. 10 also shows entrance block 160, exit block 180, as well as five rollers 202. Entrance block 160 and exit block 180 are positioned between roller die base 120 and cover plate 140, and are used to guide uncoated dental tape 250 from the entrance of coating die 110 to roller assemblies 200, and coated dental tape 252 from roller assemblies 200 to the exit of coating die 110.

Figure 11:
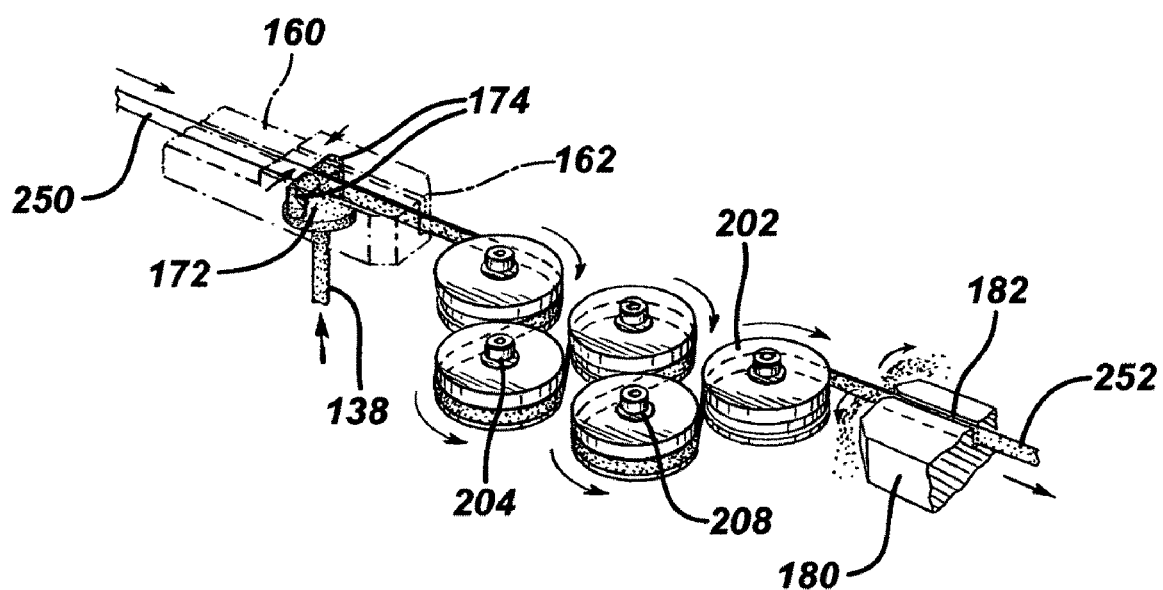
FIG. 11 is a perspective view showing movement of a vertically oriented, dental tape through the entrance and exit blocks and rollers of a roller coating die according to an exemplary embodiment of the present invention.

FIG. 11 is a perspective view showing details of how roller coating die 110 transforms uncoated elastomeric dental tape 250 to coated elastomeric dental tape 252. FIG. 11 shows uncoated dental tape 250 proceeding into entrance block 160 at a vertical orientation and travelling along entrance block slot 162. Entrance block slot 162 is sized wide enough to produce minimal tension on the vertically oriented, uncoated dental tape 250, but narrow enough that gravity does not cause the lower portion of the uncoated dental tape 250 to receive more coating than the upper portion of the uncoated tape 250. Coating travels vertically through base passage hole 138 to entrance block pool 172, and splits into two coating bores (or passages) 174. In one embodiment, uncoated dental tape 250 is coated simultaneously on both sides as it passes coating bores 174. Coated dental tape 252 then passes around rollers 202 with at least some wrap while maintained in its vertical orientation. Generally, coated dental tape 252 wraps around the rollers at from 90° to 270°. Rollers 202 assist in uniformly applying coating composition to coated dental tape 252. Though FIG. 11 shows five rollers, it is understood that coated dental tape 252 may pass around as few as one roller, or as many as about twenty or more rollers. Downstream of rollers 202 is exit block 180. Coated dental tape 252 proceeds into exit block 180 still vertically oriented and travels along exit block slot 182 which aid in maintaining the vertical orientation of dental tape 252. As mentioned above, the width 182a of exit block slot 182 is sized to provide coating composition 5 an additional opportunity to be smoothed onto the surface of coated dental tape 252 and also removes excess coating composition 5 while at the same time minimizing any additional tension caused by movement of dental tape 252 through exit block 180.

Note that all slots discussed above, including cover plate slots (144a, 144b, 144c), base slots (124a, 124b), entrance block slot 162, and exit block slot 182 may be in the form of a groove having parallel sides or walls, the groove optionally having a radius at its bottom. As will be apparent to those skilled in the art, the dimensions of the groove will depend upon such factors as the denier and type of uncoated dental tape 250 and the amount of coating composition being applied thereto.

Figure 12:
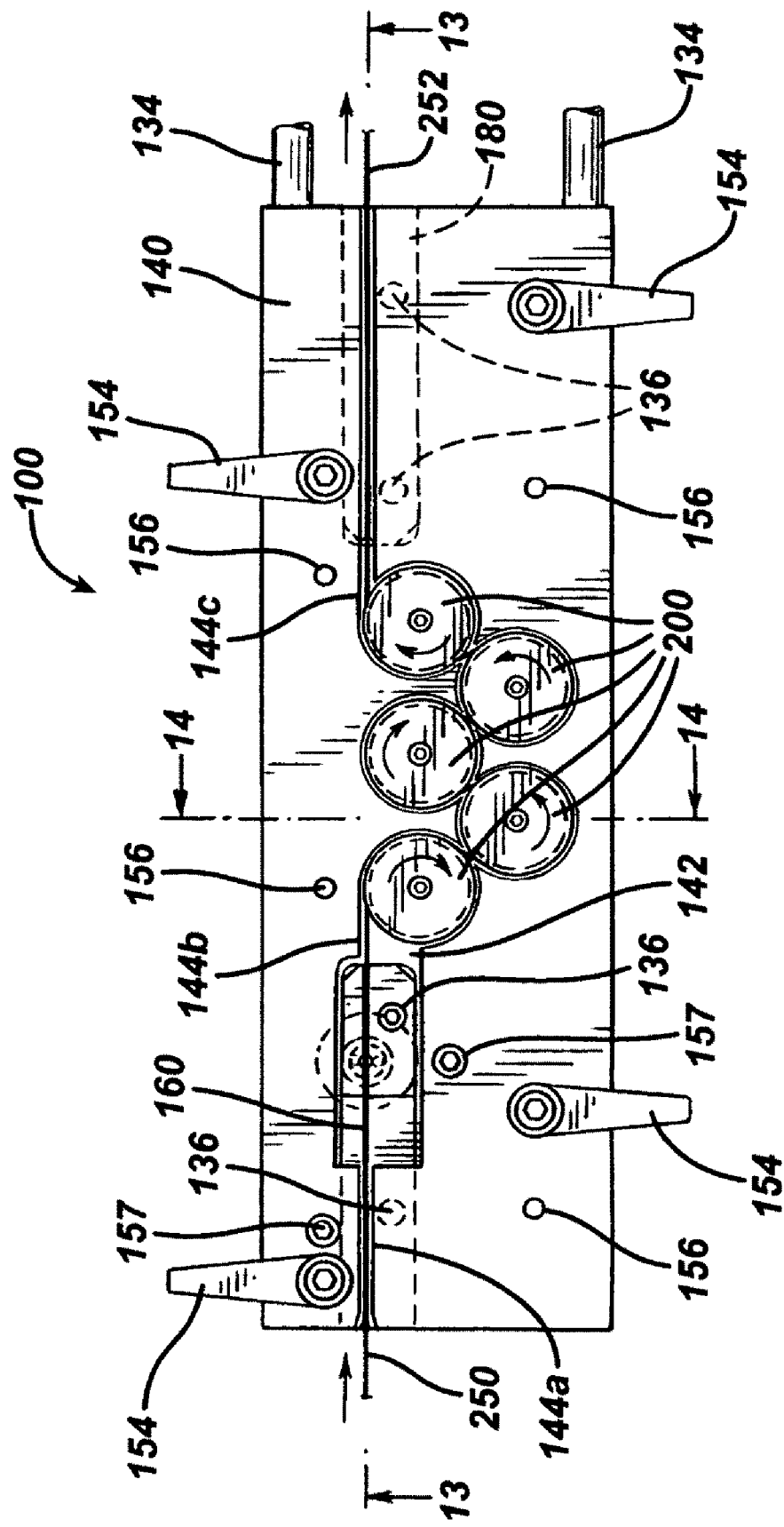
FIG. 12 is a top plan view of a roller coating die according to an exemplary embodiment of the present invention.

FIG. 12 is a top view of an embodiment of coating die 110 showing details of the cover plate 140 and the monofilament coating path. FIG. 12 shows uncoated dental tape 250 proceeding into entrance block 160 where it is coated. Coated dental tape 252 proceeds around roller assemblies 200 to exit block 180 and out of a coating die 110. Entrance block 160 is partially hidden by cover plate 140, but is visible through cover plate window 142. Roller assemblies 200 can be seen through roller wheel windows 146. Exit block 180 is hidden by cover plate 140, but coated dental tape 252 is visible through cover plate slot 144c. FIG. 12 also shows threaded handle 154, which are used to hold cover plate 140 to roller die base 120, as well as alignment holes 156 to align cover plate 140 to roller die base 120 prior to attaching the two.

Figure 13:
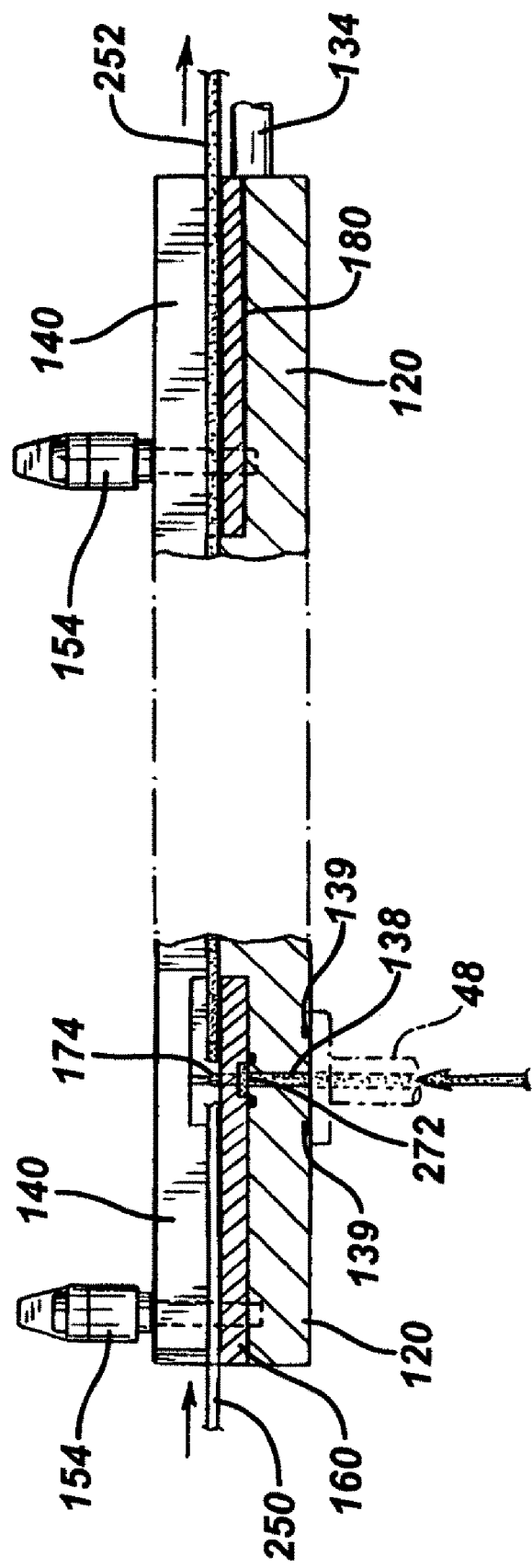
FIG. 13 is a cross-sectional view of a roller coating die according to the exemplary embodiment of FIG. 12 along the 13-13 plane.

FIG. 13 is a cross-sectional view of the coat die 110 embodiment of FIG. 12 along plane 13-13. FIG. 13 shows uncoated dental tape 250 proceeding into entrance block 160. Coating travels vertically from second pipe 48 (or coating dispensing pipe receiving coating from displacement pump 46) through base hole 138 to entrance block pool 172, and splits into two coating bores 174 (FIG. 13 shows one of the two bores). In one embodiment, uncoated dental tape 250 is coated simultaneously on both sides as it passes coating bores 174. FIG. 13 also shows coated dental tape 252 travelling through exit block 180 and out of a coating die 110. Threaded handles 154, which are used to hold cover plate 140 to roller die base 120, as well as cartridge heaters 134, which can be used if needed to keep coating composition, in a liquid state, are also shown in the figure.

FIG. 14 is a cross-sectional view of the embodiment of FIG. 12 along plane 14-14. FIG. 14 shows cover plate 140, roller die base 120, cartridge heaters 134, as well as detailed view of roller assembly 200. Roller assembly 200 includes roller 202 which assist in uniformly applying coating composition to coated dental tape 252. In certain embodiments, one end of stub shaft 210 is disposed in center of roller 202, and attached to roller 202 by cap screw 204, flat washer 206, and lock washer 208. The central portion of stub shaft 210 is disposed in inner ring shield bearing 212. The opposing end of stub shaft 210 is disposed in bearing retainer 220, and attached to bearing retainer 220 by cap screw 204, flat washer 206, and lock washer 208. Bearing retainer 220 is attached to roller die base 120 by bearing retainer cap screw 222 and bearing retainer lock washer 224. In one embodiment, three sets of cap screws 222 and lock washers 224 are used to attach bearing retainer 220 to roller die base 120. However, one skilled in the art could use more or less screws to attach the two, or other means of attachment known in the art. Finally, inner ring shield bearing 212 is kept approximately centered in roller assembly recess 126 and roller wheel window 146, by outer race spacer 214.

Figure 15:
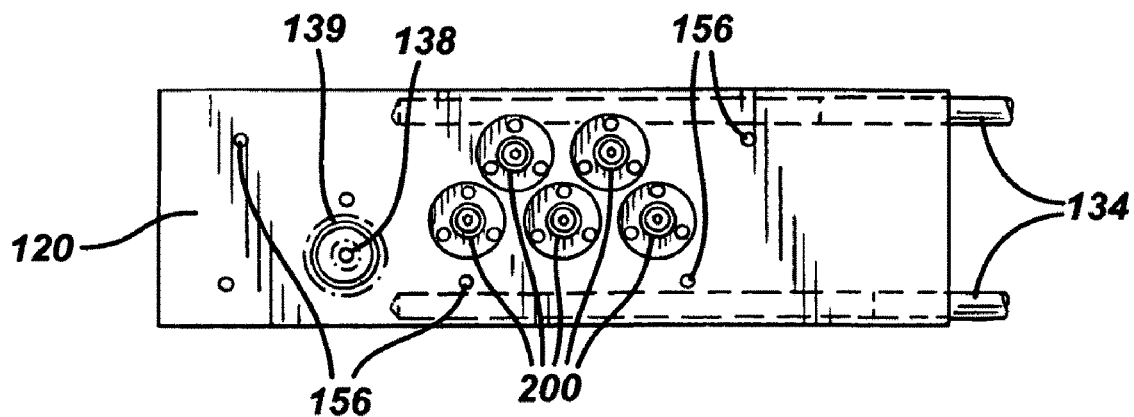
FIG. 15 is a bottom plan view of a coating die according to an exemplary embodiment of the present invention.

FIG. 15 is a bottom view of an embodiment of a roller coating die of the present invention. The FIG. 15 shows five roller assemblies 200, base hole 138, cartridge heaters 134, and alignment holes 156 on roller die base 120. An O-ring 139, is used to prevent leakage of coating composition between positive displacement pump and roller die base 120. Alignment holes 156 are used to align cover plate 140 to roller die base 120 prior to attaching the two.

FIGS. 16 through 20 show details of entrance block 160. The FIG. 16 shows entrance block slot 162 and entrance block slot guide 164. Entrance block slot guide 164 is a V-shaped or tapered cut in entrance block 160 to guide uncoated dental tape 250 into entrance block slot 162. The entrance block slot 162 is sized at a width 162a such that it maintains the vertical orientation of uncoated dental tape 250 through the entrance block 160, as well as facilitate coating as mentioned above, with little to no additional tension on the dental tape 250. Uncoated dental tape 250 travels along entrance block slot 162 to where it is coated. Coating travels vertically from entrance block pool 172 into two coating bores 174. Uncoated dental tape 250 is coated simultaneously on both sides as it passes coating bores 174. FIGS. 16 to 18 show two optional entrance block holes 166 which may be used to attach entrance block 160 to roller die base 120.

Figure 21:
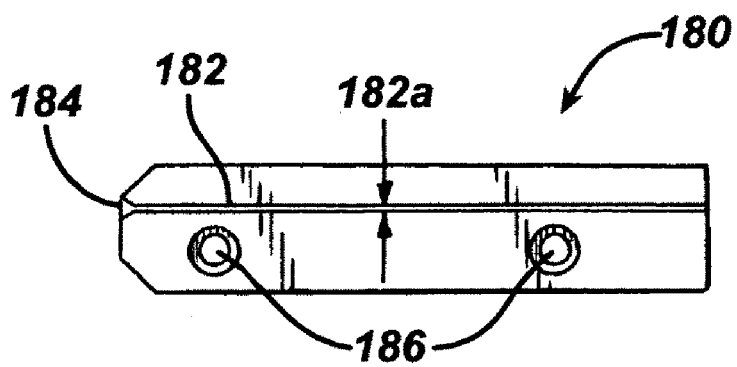
FIG. 21 is a top plan view of an exit block of a coating die according to an exemplary embodiment of the present invention.
Figure 22:
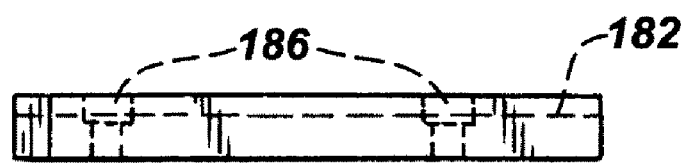
FIG. 22 is a right side elevational view of an exit block of a coating die according to an exemplary embodiment of the present invention.
Figure 23:
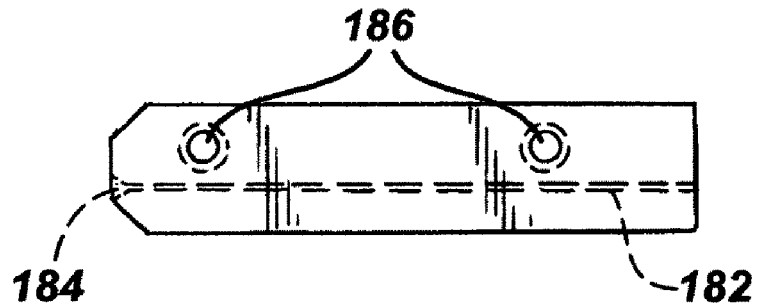
FIG. 23 is a bottom plan view of an exit block of a coating die according to an exemplary embodiment of the present invention.
Figure 24:
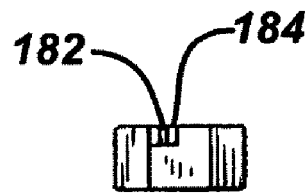
FIG. 24 is a rear elevational view of an exit block of a coating die according to an exemplary embodiment of the present invention.

FIGS. 21 through 24 show details of exit block 180. FIG. 21 shows exit block slot 182 and entrance block slot guide 184. Entrance block slot guide 184 is a V-shaped cut in exit block 180 to guide coated dental tape 252 into exit block slot 182. Exit block slot 182 allows coating composition an additional opportunity to be smoothed onto the surface of coated dental tape 252. The width 182a of exit block slot 182 is sized to provide coating composition 5 an additional opportunity to be smoothed onto the surface of coated dental tape 252 and also removes excess coating composition 5 while at the same time minimizing any additional tension caused by movement of dental tape 252 through exit block 180. Coated dental tape 252 travels along exit block slot 182 until it leaves roller coating die 110. FIGS. 21 to 23 show two optional exit block holes 186 which may be used to attach exit block 180 to roller die base 120.

While illustrated as separate components, it will be readily understood by the skilled artisan that entrance block 160 and exit block 180 (along with their distinct structural characteristics) can be integral with roller die base 120 and/or cover plate 140 without changing the performance or function of coating die 110. Maintaining entrance block 160 and exit block 180 as separate components, however, provides the convenience of interchangeability. For example, separate entrance block 160 and exit block 180 components allow for the interchange of entrance block 160 and/or exit block 180 with entrance and exit blocks of differing slot (162, 182) and slot guide (164 and 184) widths.

Coating composition 5 once applied to dental tape 10 must be solidified. Solidification can be accomplished by having a cooling area 60. Cooling area 60 can be an open area where coating 5 cools under ambient conditions. Alternatively, cooling area 60 can be a chamber where refrigerated or room air is blown over dental tape 10 to increase the rate of cooling. In order to avoid undesirable discontinuities in coating 5, dental tape 10 should not contact any surfaces until coating 5 has solidified.

Once coating 5 is cooled sufficiently to prevent any disruption of the outer surface, it is rewound on floss rewinding system 70. Rewinding system 70, shown in FIG. 8, has take-up spool 72 and speed sensing roll 74 as described before, as well as a drive motor 80, a series of timing belts (all labeled 84) and timing belt pulleys (all labeled 82), and a traversing cam guide 76 disposed on a traverse barrel cam 86. For 6 pound rolls or less, optionally 5 pounds or less, or optionally 4 pounds of less of dental tape rolled onto spool 72, the tension of the dental tape 10 is monitored using conventional tension measuring devices (such as Checkline, supplied by Electromatic Equipment Co., Cedarhurst, N.Y.) prior to rewinding and the speed adjusted accordingly such that the tension of the dental tape 10 during rewinding process is less than 300 (or about 300) grams-force, optionally less than 250, (or about 250) grams-force or optionally from about 190 grams-force to about 200 grams-force. Traversing cam guide 76 and traverse barrel cam 86 are disposed in an traversing cam guide housing 78 which has a traversing cam guide housing slot 79.

Figure 8:
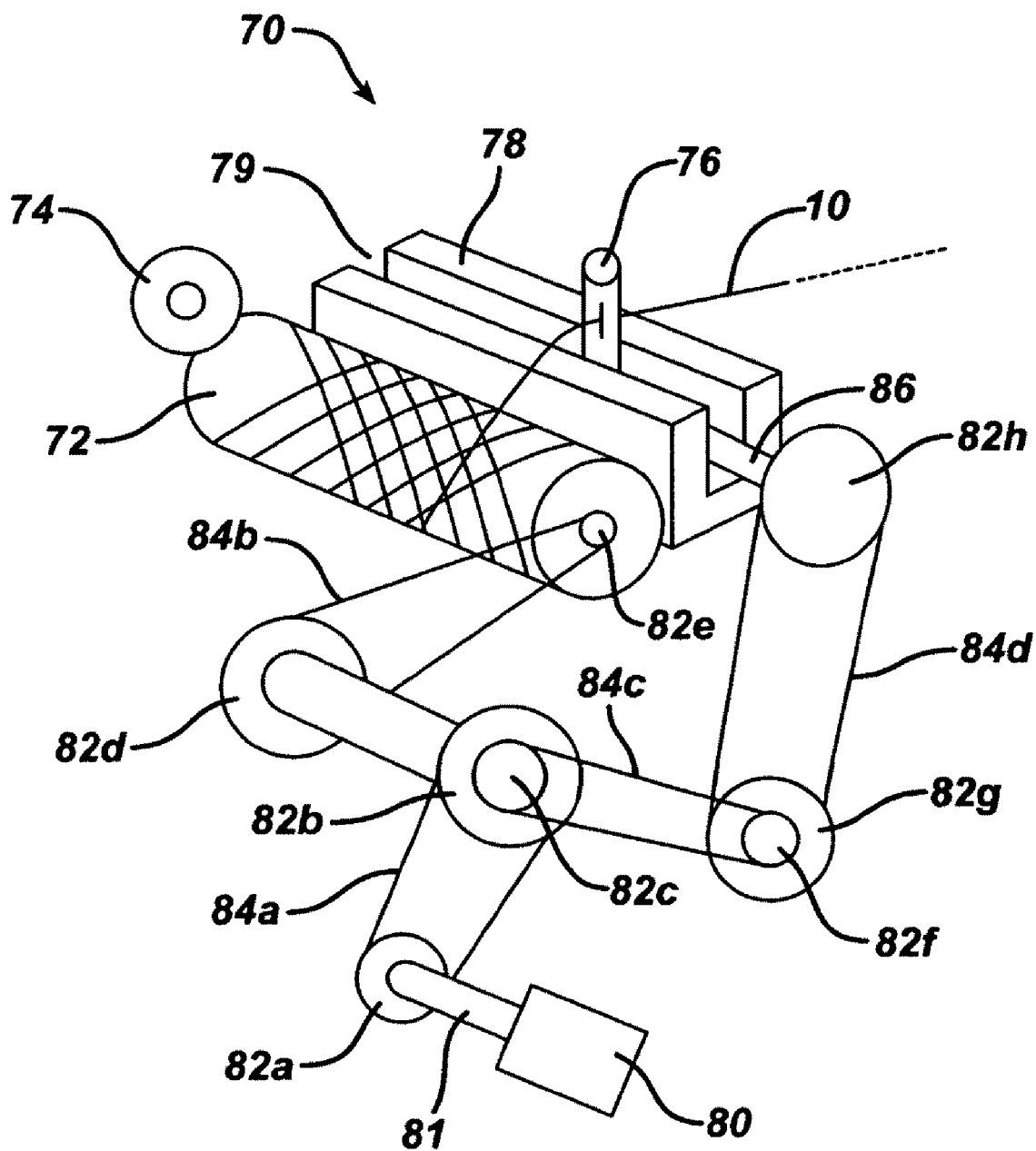
FIG. 8 is a schematic illustration of one embodiment of the rewind mechanism of the present invention.
Figure 25:
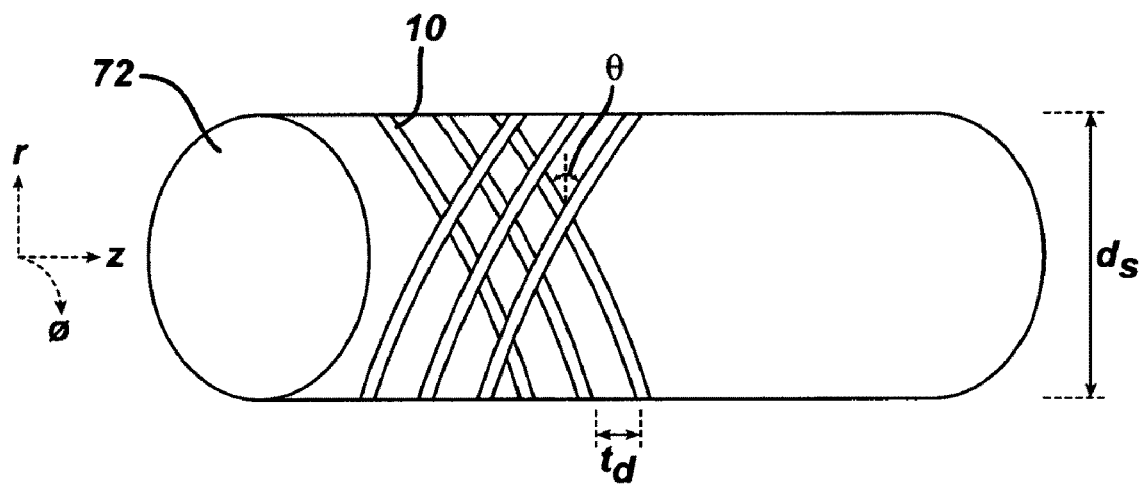
FIG. 25 is a 3 dimensional schematic illustration of one embodiment of coated roll of dental tape showing the helix angle $\theta$ formed by the strands of dental tape and the plane $r\Phi$ perpendicular to the spool's longitudinal axis z.

Rewinding system 70 is a traversing rewinder in that as take-up spool 72 rotates, traversing cam guide 76 is traversed back and forth along its length (see FIG. 8). The take-up spool 72 has a longitudinal axis z; a plane rΦ which is perpendicular to longitudinal axis z. and a circumference C (equal to the product of the spool core diameter $d_s$ and $\pi$) as shown in FIG. 25. Rewinding system 70 functions as follows: spindle 81 of motor 80 rotates to drive timing belt pulley 82a, which, through timing belt 84a, drives timing belt pulleys 82b and 82c. Timing belt pulley 82b drives timing belt pulley 82d, which, in turn, drives timing belt pulley 82e via timing belt 84b. Timing belt pulley 82e is disposed on the end of take-up spool 72, so as it rotates, take-up spool 72 rotates. Timing belt pulley 82c, via timing belt 84c, drives timing belt pulleys 82f and 82g. Timing belt pulley 82g drives timing belt pulley 82h via timing belt 84d. Timing belt pulley 82h is disposed on the end of traverse barrel cam 86, so as pulley 82h rotates, traverse barrel cam 86 rotates. Traversing cam guide 76 is disposed on traverse barrel cam 86 such that when traverse barrel cam 86 rotates, traversing cam guide 76 traverses back and forth along its length. Suitable traversing rewinders can be readily built or purchased from companies such as Leesona Corporation.

Figure 26:
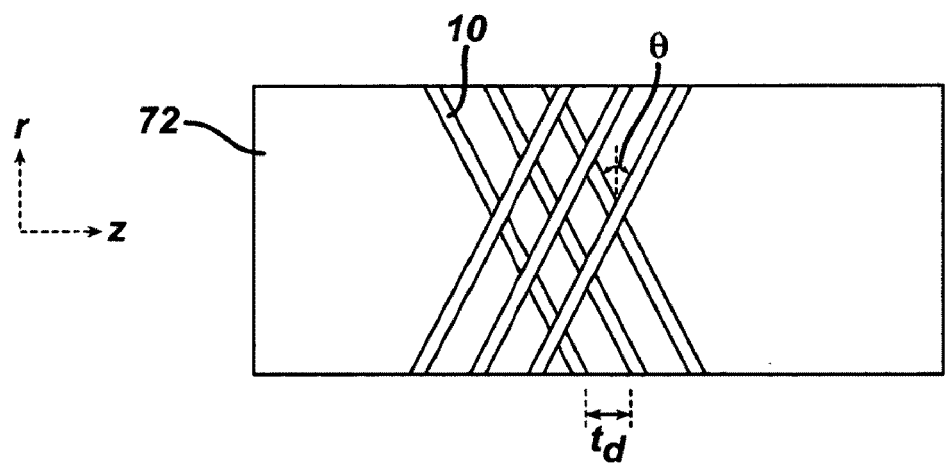
FIG. 26 is a 2 dimensional schematic illustration of one embodiment of coated roll of dental tape showing the helix angle $\theta$ formed by the strands of dental tape and side r of plane $r\Phi$ and the spacing between the individual strands of dental tape in each layer of dental tape.

In certain embodiments, the pulley sizes and traverse barrel cam are selected for the rewinding system as described below:

a.) the pulleys are selected (or adjusted) such that the product of the pulley ratios or Ratio A (which determines the traversing movement of traversing cam guide (inches) per revolution of Spool 72 (inches)) is as follows:

Ratio $A = P_1/P_2 \times P_3/P_4 \times P_{Z-1}/P_Z$

Where $P_1$ through $P_Z$ are the pulley sizes of the sequentially ordered pulleys from the pulley rotating the take-up spool 72 or $P_1$ to the pulley rotating traverse barrel cam 86 or $P_Z$ used in association with b.) the traverse barrel cam 86, which is selected such that the product of the cam advance (or, total length [end to end] traversed by traversing cam guide 76 divided by the turns of the traverse barrel cam 86 needed to achieve the total traverse of traversing cam guide 76) and Ratio A when divided by the circumference C of the core of take-up spool 72 (i.e., take-up spool 72 without tape 10) produces a Ratio B, where Ratio $B = (\text{cam advance} \times \text{Ratio } A)/\text{Circumference } C$ and where Ratio B provides a helix angle θ of from about 3.5 degrees to about 5 degrees, where the helix angle θ is formed by a strand of dental tape and plane rΦ of the spool 72 which is perpendicular to the longitudinal axis z of the spool 72 as shown in FIGS. 25 and 26 and is determined by formula:

$\sin^{-1}(\text{Helix Angle } \theta) = \text{Ratio } B$

Without being limited by theory, it is believed that obtaining a helix angle θ of about 3.5 degrees to about 5.5 degrees provides take-up spool rolls 72 of dental tape 10 such that:

i) in any given layer of the dental tape, the strands of dental tape 10 forming that layer do not overlap, or optionally do not touch or optionally have a space therebetween $t_s$ of up to 1/32 (or about 1/32) of an inch and ii.) the strands of dental tape 10 forming each layer of dental tape 10 overlap with the strands of dental tape 10 forming the preceding layer of dental tape 10 to form intersection angles of about 7 to about 11 degrees (or twice the helix angle θ)

If it is desired to apply a second coating to dental tape 10, this may be done by locating another coating line and cooling chamber downstream of cooling area 60.

Figure 27:
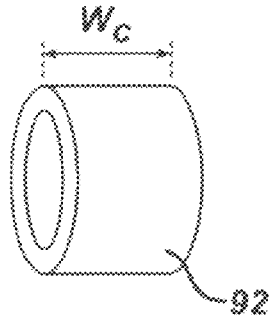
FIG. 27 is a perspective view of a bobbin spool core.
Figure 28A:
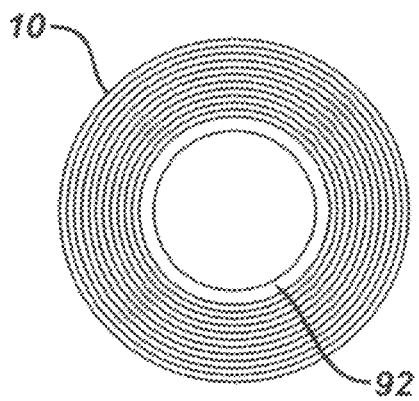
FIG. 28$a$ is right side elevational view of a tape bobbin with tape wound around the bobbin spool core.
Figure 28B:
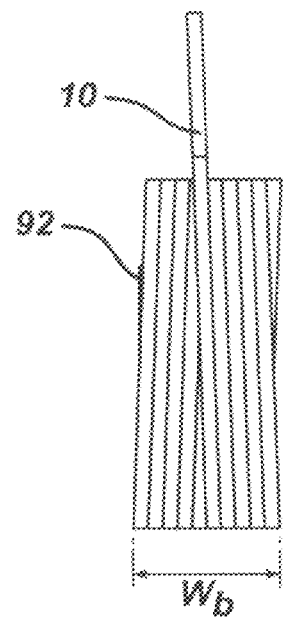
Figure 29A:
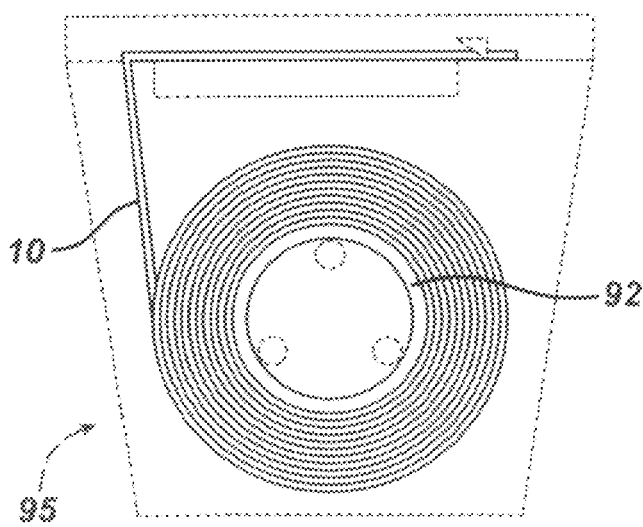
FIG. 29$a$ right side elevational view of a tape bobbin movably positioned within a dispenser (phantom lined).
Figure 29B:
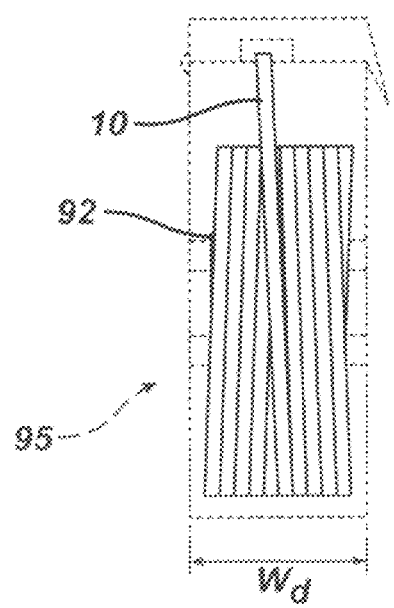

In certain embodiments, spool 72 dental tape 10 is then removed for later processing into bobbins 90. Bobbins of tape as shown in FIGS. 28a and 28b are formed from dental tape 10 unwound from spool 72 onto bobbin spool cores 92 of selected width $w_c$ as shown in FIG. 27 and packaged into dispensers 95 of selected width $w_d$ for use by consumers as shown in FIGS. 23a and 23b. In certain embodiments, the bobbin spool cores 92 have an aspect ratio of greater than about 2:1, optionally about 3:1, where the aspect ratio is the ratio of bobbin spool diameter to width. The dental tape 10 winds from spool 72 onto the bobbin spool cores 92 to form tape bobbins where the wound tape widths $w_b$ such that wound tape width $w_b$ exceeds the width of the bobbin spool core $w_c$ by no more that 10% (or about 10%), optionally, 5% (or about 5%), optionally 2.5% (or about 2.5%), optionally 1% (or about 1%). Hence, the inventive rewinding system 70 which produces helix angles θ of from about 3.5 degrees to about 5.5 degrees ensures that the wound tape widths $w_b$ of the finished tape bobbins formed from spool 72 do not telescope so as to interfere with the packaging of the finished tape bobbin into dispensers 95 specifically designed to movably accommodate bobbin spool cores 92 of widths $w_c$. More generally, the inventive rewinding system 70 permits the use of narrower width dispensers particularly in cases where the tape or floss is made of an elastomeric material.

EXAMPLES

Dental tapes illustrated in following examples illustrate specific embodiments of the dental tapes of the present invention, but are not intended to be limiting thereof. Other modifications can be undertaken by the skilled artisan without departing from the spirit and scope of this invention.

Example 1

Dental tape of the invention was produced using PEBAX MX 1205 resin. The resin was dried for over 3 hours at 75° C., fed into a Haake 20 mm extruder with a Slack and Parr gear melt pump attached and extruded through a shaped die formed of stainless steel, and having a cross-section similar to that of the dental tape shown in FIG. 1. The extruded dental tape included eleven ribs protruding from both the first and second cleaning surfaces. The overall width of the slot ($w_t$) was 0.303 inches. The thickness of the core body of the die ($t_c$) was 0.0035 inches. The height and width of the rib portions of the die ($h_r$ and $w_r$) were 0.0075 inches and 0.0035 inches, respectively. The spacing between neighboring ribs on both cleaning surfaces ($s_r$) was 0.026 inches, and the ratio of $s_{ar}$ to $s_r$ was 0.5, i.e. the ribs on the second cleaning surface were positioned about midway between those on the first cleaning surface.

The extruded tape passed through a room temperature water bath and was wound on a spool.

One extrusion was performed using the shaped die to prepare the dental of the invention. For comparison, two extrusions were performed through a flat die to prepare comparative dental tapes with no ribs. For Run 2, the die thickness and width were 0.085 inches and 0.490 inches, respectively. For Run 3, the die thickness and width were 0.012 inches and 0.350 inches, respectively.

The conditions for the three extrusions are shown on Table I:

TABLE I

| Extrusion conditions. | | | |
|---|---|---|---|
| | Run 1 | Run 2 | Run 3 |
| Die | shaped | flat | flat |
| Barrel T (Zones 1-6), ° C. | 195 | 220 | 213 |
| Die T, ° C. | 203 | 233 | 216 |
| Flow rate, cc/min | 4.8 | 4.3 | 6.4 |
| Die to water bath, inches | 1 | 3 | 7 |
| Take-up speed, feet/min | 20 | 24 | 24 |

The tapes from the three extrusion runs were subjected to drawing operations to produce the final dental tapes. In the drawing operation, the tape was unwound from the spool, passed over a heated roller, across a hot plate, and rewound on a second roller. Conditions for the three drawing runs are shown on Table II:

TABLE II

| Drawing conditions. | | | |
|---|---|---|---|
| | Run 1 | Run 2 | Run 3 |
| Roll 1 T, ° C. | 60 | 60 | 60 |
| Plate T, ° C. | 100 | 90 | 60 |
| Roll 1 Speed, meter/min | 2 | 2 | 2 |
| Roll 2 Speed, meter/min | 18 | 14 | 12 |
| Draw ratio | 9 to 1 | 7 to 1 | 6 to 1 |

Some of the tape from Run 1 was coated with a microcrystalline wax, W445 supplied by Crompton (Petrola, Pa.). This tape was designated as Run 1a. To coat the tape, the tape was pulled through a bath containing the wax at 88° C. Upon leaving the bath, excess wax was removed. The average weight of wax applied was 52% of the weight of the final tape.

The overall width, thickness, and denier of the tapes were measured and are summarized on Table III:

TABLE III

Tape dimensions.

|  | Run 1 | Run 1a | Run 2 | Run 3 |
|---|---|---|---|---|
| Width, inches | 0.075 | 0.080-0.090 | 0.073 | 0.072 |
| Thickness, inches | 0.005 | 0.006-0.008 | 0.005 | 0.002 |
| Denier | 1008 | NA | 1586 | 861 |

The compression and recovery expansion of the tapes made above were measured using an apparatus comprised of 2 steel shafts that are used to simulate two adjacent teeth surfaces. One of the steel shafts was stationary, while the other shaft pivoted. A thickness indicator was set to zero when the moving shaft was resting on the fixed shaft. The tape was placed at a ninety-degree angle to the axis of the stationary shaft. The moveable shaft, constructed so as to exert little pressure on the nip point, was allowed to rest on top of the tape, and the original thickness ($t_o$) reading was taken from the indicator. Next, a one-pound weight was applied directly above the nip point, and the compressed thickness ($t_c$) reading was recorded. The percent compression was calculated as Percent Compression=$100 \times (t_o-t_c)/t_o$ A measure of the recovery expansion of the tape was obtained using this device by removing all force and noting the recovery thickness ($t_r$) reading on the indicator. The percent recovery was calculated as:

Percent Recovery=$100 \times (t_r-t_c)/(t_o-t_c)$

The percent compression and percent recovery of each of the tapes were measured, and the results are summarized on Table IV:

TABLE IV

Tape compression and recovery.

|  | Run 1 | Run 1a | Run 2 | Run 3 |
|---|---|---|---|---|
| Original Thickness, inches | 0.005 | 0.006-0.008 | 0.005 | 0.002 |
| Compression, % | 70 | 54 | 31 | 25 |
| Recovery, % | 67 | 52 | 93 | 100 |

Next, the tensile properties and tenacity of the tapes were measured using an Instron universal testing machine with a specimen length of 10 inches, and a cross-head speed of 10 inches per minute.

The tensile strength, percent elongation at break and tenacity of each of the tapes were measured, and the results are summarized on Table V:

TABLE V

Tape tensile properties.

|  | Run 1 | Run 1a | Run 2 | Run 3 |
|---|---|---|---|---|
| Tensile strength, lbs | 7.5 | 8.1 | 9.8 | 6.5 |
| Elongation at Break, % | 64 | 165 | 87 | 52 |
| Tenacity, grams/denier | 3.7 | 3.6 | 2.8 | 3.1 |

A comparison of the cleaning ability of a number of flosses and tapes was next conducted. The process used is summarized in a paper by Yankel, S. L., et al., "Laboratory Evaluations of Three Dentifrices with Polishing or Brushing", Journal of Clinical Dentistry, 9(3):61-63 (1998). In short, the wet pressure-sensitive paper described in Yankel was placed on the ⅜"-diameter upright shaft. The floss or tape being tested was strung through the eyelets, which pulled the floss back 0.100 inch on either side of the shaft. The eyelets were located equal distance and 1 inch from the centerline of the shaft. A tension of approximately 250 grams force was placed on the floss. The floss was wetted with deionized water from a spray bottle, and the tape or floss was passed up and down on the paper (¾-inch stroke distance), abrading the paper fibers and exposing the various colored surfaces. The paper was removed after 5 cycles and saved for comparison. The Depth of Deposit Removal (DDR) was recorded using a 0-4 scale from a comparative color chart.

The tape from Run 1, made as discussed above, was tested, as were two commercially available dental flosses. The commercially available dental flosses were a monofilament coated floss sold under the trade name GLIDE ORIGINAL (Proctor & Gamble, Cincinnati, Ohio), and a wax-coated multifilament floss sold under the trade name REACH MINT WAXED (PPC Division of McNeil-PPC, Inc. Skillman, N.J.).

Figure 6A:
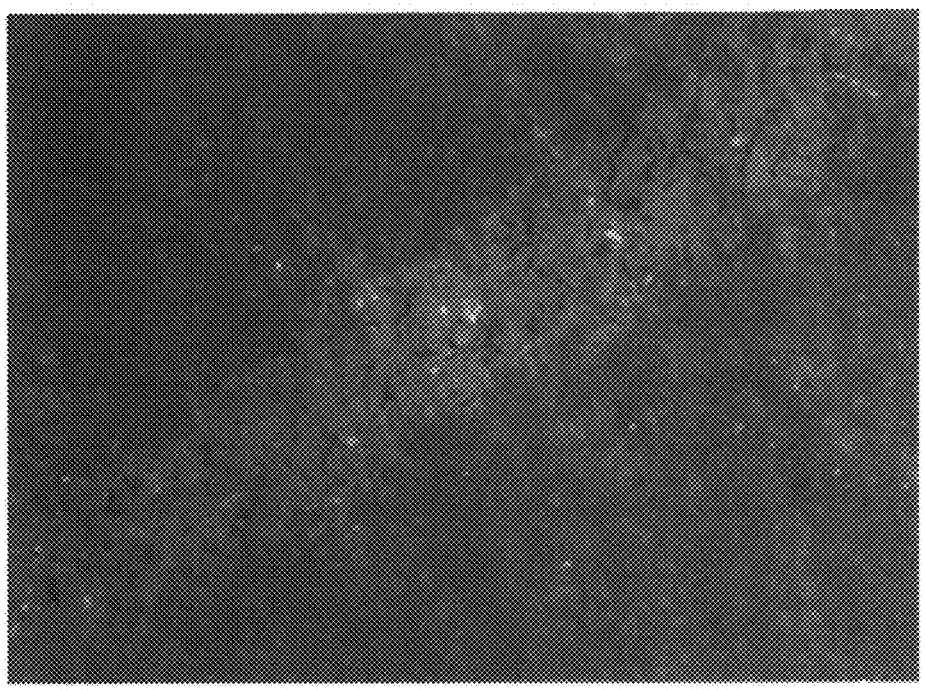
FIGS. 6a-6c are photographs (50×) of wet pressure sensitive papers after performance of depth of deposit removal (DDR) assessment for several dental tapes.
Figure 6B:
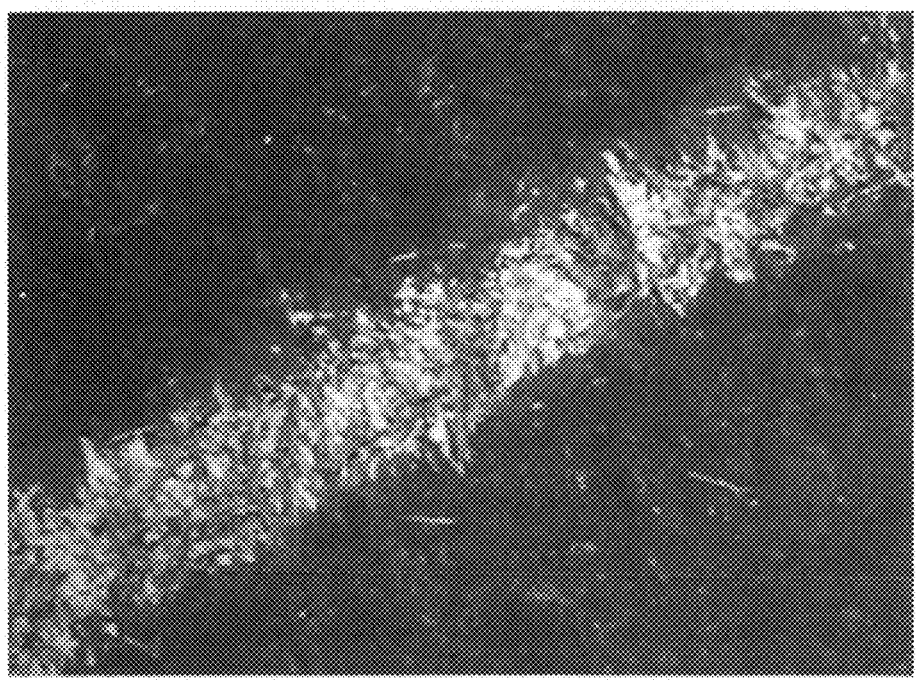
Figure 6C:
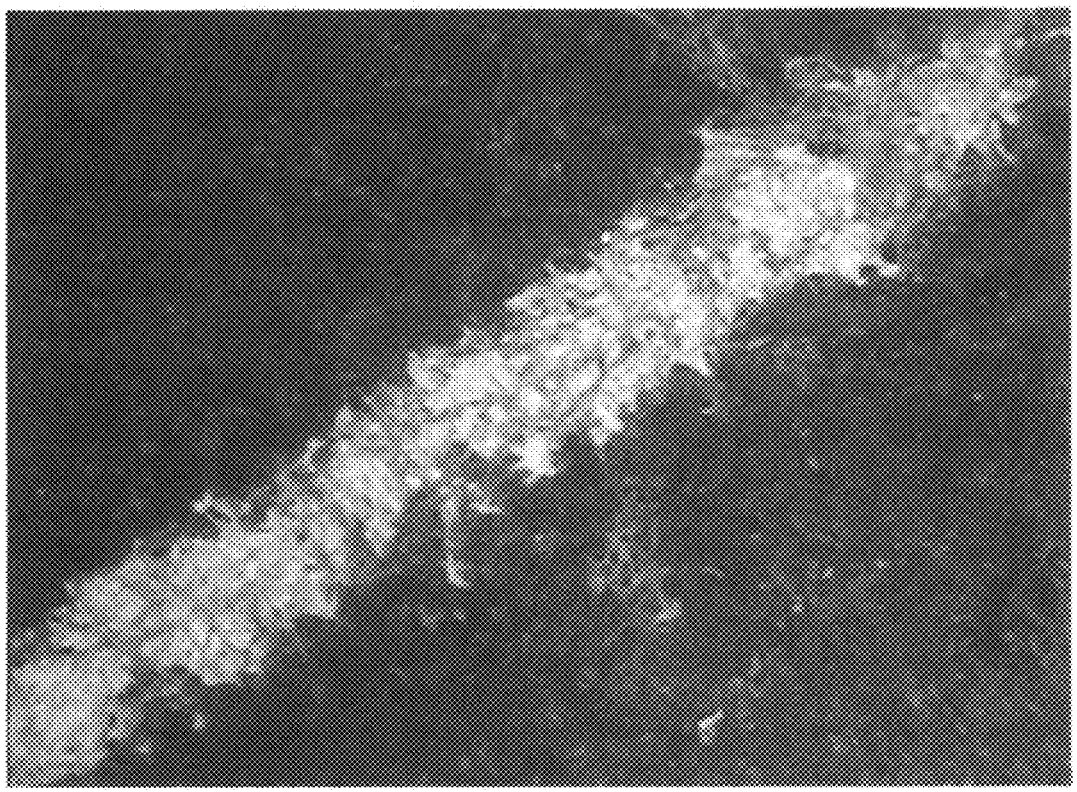

FIGS. 6a-6c are photographs of wet pressure sensitive papers after performance of depth of deposit removal (DDR) assessment described above for the noted dental flosses and tapes. The images are at magnifications of 50×. The flossing pattern is diagonal with respect to the image from the top right to bottom left. Table VI shows a comparison of the Depth of Deposit Removal (DDR) values for the tapes tested.

TABLE VI

Depth of Deposit Removal (DDR) for Noted Flosses and Tapes

| Floss/Tape | DDR | FIG. |
|---|---|---|
| REACH MINT WAXED | 1.0 | 6b |
| GLIDE ORIGINAL | 0.25 | 6a |
| Run 1 | 1.25 | 6c |

The results showed that the ribbed dental tape of the invention performed as well as or somewhat better than the multifilament REACH MINT WAXED floss, and superior to the monofilament GLIDE ORIGINAL floss.

Finally, a comparison of the toughness of a number of tapes and flosses was conducted. In brief, a toughness tester as described in U.S. Pat. No. 5,908,039 (FIGS. 3 and 4), which is incorporated by reference herein, was used. Rather than using teeth in this test, two metal posts were used to replace teeth, shown in FIG. 4 of U.S. Pat. No. 5,908,039. Item 21 was a steel cylinder, 0.375 inch diameter by 0.725 long with a threaded surface. The thread was 0.01 inches deep with a pitch of 0.02 inches. This represents a rough, although not sharp, surface. Item 22 was a conical smooth cylinder, 0.725 inches long. The base of the cone was 0.15 inches in diameter. The cone diameter increased to 0.375 inched in diameter over a length of 0.57 inches, and remained 0.375 inches for 0.025 inches. The diameter then decreased to 0.125 over the remaining length. A spring force, item 24, was set to exert 1.75-lbs force on tooth 22. The floss or tape to be tested was strung between the simulated teeth. The floss or tape was held with a tension of approximately 250 grams force and the cylinders were move up and down. This was repeated until the tape or floss broke. The test was repeated ten times on each of the tapes or flosses being tested.

The tapes from Runs 1, 1a, and 2, made as discussed above, were tested, as were commercially available dental flosses. The commercially available dental flosses were GLIDE ORIGINAL, GLIDE COMFORT, a lightly waxed monofilament flosses, and REACH MINT WAXED.

A comparison of the cycles to failure for each of the tapes and flosses tested are summarized on Table VII:

TABLE VII

Cycles to Failure for Various Flosses and Tapes

| Floss | Average |
|---|---|
| Mint Waxed | 4.8 |
| Glide Original | 7.6 |
| Glide Comfort | 4.7 |
| Run 1 | 8.2 |
| Run 1a | 10.3 |
| Run 2 | 2.4 |

Table VII shows the floss of Run 1a has higher average cycle to failure than all others. Run 2 used the same material as Run 1 and 1a, but with a flat cross-section. Surprisingly, Run 1 exhibited a significantly higher cycle to failure than Run 2. While not intending to be bound by the theory, it is believed that the presence of ribs along the surface of the core body of the monofilament tape protects the monofilament tape from shredding, thereby providing a dental tape that not only cleans better than a tape without ribs, as shown in Table VI, but that is stronger and more resistant to shredding.

Example 2

Dental tape of the invention was produced using several other resins. The resins used are listed on Table VIII.

TABLE VIII

| | Resin |
|---|---|
| Run 4 | HYTREL 4056 |
| Run 5 | HYTREL 4056 |
| Run 6 | PELLETHANE 2363-90AE |
| Run 7 | MULTIFLEX 1047S |
| Run 8 | TECOFLEX EG-100A |

The resins were dried for over 3 hours at 75° C. They were processed in the extruder of Example 1, using the ribbed die described in Example 1.

The conditions for the extrusions are shown on Table IX:

TABLE IX

| Extrusion conditions. | | | | | |
|---|---|---|---|---|---|
| | Run 4 | Run 5 | Run 6 | Run 7 | Run 8 |
| Barrel T (Zones 1-6), ° C. | 230 | 225 | 200 | 260 | 187 |
| Die T, ° C. | 239 | 235 | 202 | 262 | 189 |
| Flow rate, cc/min | NA | NA | 3.2 | 4.3 | 3.2 |
| Die to water bath, inches | 1 | 4 | 2.5 | 8 | 4 |
| Take-up speed, feet/min | 20 | 20 | 20 | 14 | 17 |

The tapes from the extrusion runs were drawn following the procedure of Example 1. Conditions for the three drawing runs are shown on Table X:

TABLE X

| Drawing conditions. | | | | | |
|---|---|---|---|---|---|
| | Run 4 | Run 5 | Run 6 | Run 7 | Run 8 |
| Roll 1 T, ° C. | cold | cold | 50 | 55 | 70 |
| Plate T, ° C. | 100 | 100 | 90 | 115 | 70 |
| Roll 1 Speed, meter/min | 2 | 2 | 2 | 2 | 2 |
| Roll 2 Speed, meter/min | 16 | 15 | 14 | 12 | 16 |
| Draw Ratio | 8 to 1 | 7.5 to 1 | 7 to 1 | 6 to 1 | 8 to 1 |

The overall width, thickness, and denier of the tapes were measured, and are summarized on Table XI:

TABLE XI

| Tape dimensions. | | | | | |
|---|---|---|---|---|---|
| | Run 4 | Run 5 | Run 6 | Run 7 | Run 8 |
| Width, inches | 0.080 | 0.080 | 0.090 | 0.070 | 0.060 |
| Thickness, inches | 0.0065 | 0.0065 | 0.0065 | 0.007 | 0.0045 |

The tensile properties of the tapes were measured as described in Example 1. The tensile strength and percent elongation at break are summarized on Table XII:

TABLE XII

| Tape tensile properties. | | | | | |
|---|---|---|---|---|---|
| | Run 4 | Run 5 | Run 6 | Run 7 | Run 8 |
| Tensile strength, lbs | 9.5 | 8.7 | 7.6 | 3.1 | 3.5 |
| St. Dev. | 0.3 | 0.6 | 0.4 | 0.2 | 0.4 |
| Elongation at Break, % | 102 | 87 | 105 | 25 | 68 |
| St. Dev. | 4 | 5 | 10 | 6 | 6 |

Example 3

Dental tape of the invention was produced using PEBAX MX 1205 resin where the drawing conditions were modified to change the dimensions of the final tape. The resins were dried for over 3 hours at 75° C., and processed in the extruder of Example 1, using the ribbed die described in Example 1.

The conditions for the extrusions are shown on Table XIII:

TABLE XIII

| Extrusion conditions. | | | |
|---|---|---|---|
| | Run 9 | Run 10 | Run 11 |
| Barrel T (Zones 1-6), ° C. | 205 | 195 | 210 |
| Die T, ° C. | 207 | 197 | 212 |
| Flow rate, cc/min | 3.2 | 3.2 | 3.2 |
| Die to water bath, inches | 6 | 2 | 1.5 |
| Take-up speed, feet/min | 22 | 22 | 22 |

The tapes from the extrusion runs were drawn following the procedure of Example 1. Conditions for the three drawing runs are shown on Table XIV:

TABLE XIV

| Drawing conditions. | | | |
|---|---|---|---|
| | Run 9 | Run 10 | Run 11 |
| Roll 1 T, ° C. | cold | cold | 50 |
| Plate T, ° C. | 80 | 80 | 80 |
| Roll 1 Speed, meter/min | 2 | 2 | 2 |
| Roll 2 Speed, meter/min | 18 | 18 | 18 |
| Draw Ratio | 9 to 1 | 9 to 1 | 9 to 1 |

The overall width, thickness, and denier of the tapes were measured, and are summarized on Table XV:

TABLE XV

| Tape dimensions. | | | |
|---|---|---|---|
| | Run 9 | Run 10 | Run 11 |
| Width, inches | 0.055 | 0.055 | 0.060 |
| Thickness, inches | 0.0035 | 0.0035 | 0.0045 |

The tensile properties of the tapes were measured as described in Example 1. The tensile strength and percent elongation at break are summarized on Table XVI:

TABLE XVI

| Tape tensile properties. | | | |
|---|---|---|---|
| | Run 9 | Run 10 | Run 11 |
| Tensile strength, lbs | 6.4 | 6.6 | 5.0 |
| St. Dev. | 0.1 | 0.5 | 0.5 |
| Elongation at Break, % | 37 | 34 | 138 |
| St. Dev. | 4 | 6 | 10 |

Example 4

Dental tape of the invention was produced using PEBAX MX 1205, 3533, and 2533 resins. The resins were dried for over 3 hours at 75° C., and processed in the extruder of Example 1, using the ribbed die described in Example 1.

The conditions for the extrusions are shown on Table XVII:

TABLE XVII

| Extrusion conditions. | | | |
|---|---|---|---|
| | Run 1 | Run 12 | Run 13 |
| PEBAX Resin | MX 1205 | 3533 | 2533 |
| Barrel T (Zones 1-6), ° C. | 195 | 220 | 200 |
| Die T, ° C. | 203 | 222 | 202 |
| Flow rate, cc/min | 4.8 | 4.8 | 4.8 |
| Die to water bath, inches | 1 | 4 | 3 |
| Take-up speed, feet/min | 20 | 17 | 18 |

The tapes from the extrusion runs were drawn following the procedure of Example 1. Conditions for the three drawing runs are shown on Table XVIII:

TABLE XVIII

| Drawing conditions. | | | |
|---|---|---|---|
| | Run 1 | Run 12 | Run 13 |
| Roll 1 T, ° C. | 60 | 60 | 70 |
| Plate T, ° C. | 100 | 100 | 85 |
| Roll 1 Speed, meter/min | 2 | 1 | 2 |
| Roll 2 Speed, meter/min | 18 | 9 | 17 |
| Draw Ratio | 9 to 1 | 9 to 1 | 8.5 to 1 |

The overall width, thickness, and denier of the tapes were measured, and are summarized on Table XIX:

TABLE XIX

| Tape dimensions. | | | |
|---|---|---|---|
| | Run 1 | Run 12 | Run 13 |
| Width, inches | 0.075 | 0.080 | 0.080 |
| Thickness, inches | 0.005 | 0.0055 | 0.005 |

The tensile properties of the tapes were measured as described in Example 1. The tensile strength and percent elongation at break are summarized on Table XX:

TABLE XX

| Tape tensile properties. | | | |
|---|---|---|---|
| | Run 1 | Run 12 | Run 13 |
| Tensile strength, lbs | 7.5 | 6.1 | 4.8 |
| Elongation at Break, % | 64 | 142 | 194 |

Example 5

Dental tape of the invention was produced using PEBAX MX 1205 resin where the number of ribs was modified to change the structure of the final tape.

The die was formed of stainless steel, and had a cross-section similar to that in Example 1. The difference is that in Example 1, there were eleven ribs protruding from both the first and second cleaning surfaces. Here, there were five ribs protruding from both the first and second cleaning surfaces. The overall width of the slot, or $w_t$, was 0.305 inches. The thickness of the core body of the die $t_c$ was 0.0035 inches. The height and width of the rib portions of the die ($h_r$ and $w_r$, respectively) were 0.0075 inches and 0.0035 inches. The spacing between neighboring ribs both cleaning surfaces was ($s_r$) is 0.050 inches, and the ratio of $s_{ar}$ to $s_r$ is 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XXI:

TABLE XXI

| Extrusion conditions. | | |
|---|---|---|
| | Run 1 | Run 14 |
| Number of Ribs | 22 | 10 |
| Barrel T (Zones 1-6), ° C. | 195 | 195 |
| Die T, ° C. | 203 | 196 |
| Flow rate, cc/min | 4.8 | 4.3 |
| Die to water bath, inches | 1 | 2 |
| Take-up speed, feet/min | 20 | 23 |

The tapes from the extrusion runs were drawn following the procedure of Example 1. Conditions for the three drawing runs are shown on Table XXII:

TABLE XXII

Drawing conditions.

|  | Run 1 | Run 14 |
| --- | --- | --- |
| Roll 1 T, ° C. | 60 | Cold |
| Plate T, ° C. | 100 | 80 |
| Roll 1 Speed, meter/min | 2 | 2 |
| Roll 2 Speed, meter/min | 18 | 17 |
| Draw Ratio | 9 to 1 | 8.5 to 1 |

The tape was coated with a microcrystalline wax, W445, as described in Example 1, where the coated tape was designated as Run 1a.

The compression and recovery expansion of the tapes was measured as described in Example 1. The percent compression and percent recovery of each of the tapes were measured, and the results are summarized on Table XXIII:

TABLE XXIII

Tape compression and recovery.

|  | Run 1a | Run 14 |
| --- | --- | --- |
| Original Thickness, inches | 0.007 | 0.007 |
| Compression, % | 58 | 61 |
| Recovery, % | 42 | 78 |

The toughness of the tapes was conducted by measuring the cycles to failure for each of the tapes as described in Example 1. The results are summarized on Table XXIV:

TABLE XXIV

Cycles to Failure for Tapes

| Tape | Average |
| --- | --- |
| Run 1a | 10.3 |
| Run 14 | 4.7 |

While utilizing fewer ribs per cleaning surface may provide as dental tape that is not as strong as one having greater than about 8 per surface, for example 10 or greater, Run 14 demonstrates that having a plurality of ribs disposed along both cleaning surfaces of dental tape improves strength when compared to a dental tape having no ribs, as seen in Run 2, Table VI.

Example 6

Dental tape of the invention was produced using PEBAX MX 1205 resin where the width of ribs was modified to change the structure and dimensions of the final tape.

The die was formed of stainless steel, and had a cross-section similar to that in Example 1. There were eleven ribs protruding from both the first and second cleaning surfaces. The overall width of the slot, or $w_t$, was 0.303 inches. The thickness of the core body of the die $t_c$ was 0.0035 inches. The height and width of rib portions of the die ($h_r$ and $w_r$, respectively) were 0.0075 inches and 0.0025 inches. In Example 1, the width of rib portions of the die ($w_r$) was 0.0035 inches. The spacing between neighboring ribs both cleaning surfaces is ($s_r$) was 0.026 inches, and the ratio of $s_{ar}$ to $s_r$ was 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XXV:

TABLE XXV

Extrusion conditions.

|  | Run 1 | Run 15 |
| --- | --- | --- |
| Width of Ribs, inches | 0.0035 | 0.0025 |
| Barrel T (Zones 1-6), ° C. | 195 | 193 |
| Die T, ° C. | 203 | 193 |
| Flow rate, cc/min | 4.8 | 4.3 |
| Die to water bath, inches | 1 | 2 |
| Takeup speed, feet/min | 20 | 20 |

The tapes from the extrusion runs were drawn following the procedure of Example 1. Conditions for the three drawing runs are shown on Table XXVI:

TABLE XXVI

Drawing conditions.

|  | Run 1 | Run 14 |
| --- | --- | --- |
| Roll 1 T, ° C. | 60 | Cold |
| Plate T, ° C. | 100 | 85 |
| Roll 1 Speed, meter/min | 2 | 2 |
| Roll 2 Speed, meter/min | 18 | 18 |
| Draw Ratio | 9 to 1 | 9 to 1 |

The tape was coated with a microcrystalline wax, W445, as described in Example 1, where the coated tape was designated as Run 1a.

The compression and recovery expansion of the tapes was measured as described in Example 1. The percent compression and percent recovery of each of the tapes were measured, and the results are summarized on Table XXVII:

TABLE XXVII

Tape compression and recovery.

|  | Run 1a | Run 15 |
| --- | --- | --- |
| Original Thickness, inches | 0.007 | 0.006 |
| Compression, % | 54 | 63 |
| Recovery, % | 52 | 77 |

The toughness of the tapes was conducted by measuring the cycles to failure for each of the tapes as described in Example 1. The results are summarized on Table XXVIII:

TABLE XXVIII

Cycles to Failure for Tapes

| Tape | Average |
| --- | --- |
| Run 1a | 10.3 |
| Run 15 | 10.0 |

Example 7

Dental tape of the invention is produced using PEBAX MX 1205 resin where the height of the ribs was modified to change the structure and dimensions of the final tape.

The die is formed of stainless steel, and had a cross-section similar to that in Example 1. There were eleven ribs protruding from both the first and second cleaning surfaces. The overall width of the slot, or $w_t$, was 0.303 inches. The thickness of the core body of the die $t_c$ was 0.0035 inches. The height and width of the rib portions of the die ($h_r$ and $w_r$, respectively) were 0.0038 inches and 0.0035 inches. In Example 1, the height of rib portions of the die ($h_r$) was 0.0075 inches. The spacing between neighboring ribs both cleaning surfaces is ($s_r$) was 0.026 inches, and the ratio of $s_{ar}$ to $s_r$ was 0.5, i.e. the ribs on second cleaning surface were positioned about midway between those on first cleaning surface.

The resin was dried for over 3 hours at 75° C., and processed in the extruder of Example 1. The conditions for the extrusions are shown on Table XXIX:

TABLE XXIX

Extrusion conditions.

|  | Run 1 | Run 16 |
|---|---|---|
| Height of Ribs, inches | 0.0075 | 0.0038 |
| Barrel T (Zones 1-6), ° C. | 195 | 197 |
| Die T, ° C. | 203 | 199 |
| Flow rate, cc/min | 4.8 | 4.3 |
| Die to water bath, inches | 1 | 2 |
| Take-up speed, feet/min | 20 | 20 |

The tapes from the extrusion runs were drawn following the procedure of Example 1. Conditions for the three drawing runs are shown on Table XXX:

TABLE XXX

Drawing conditions.

|  | Run 1 | Run 14 |
|---|---|---|
| Roll 1 T, ° C. | 60 | Cold |
| Plate T, ° C. | 100 | 85 |
| Roll 1 Speed, meter/min | 2 | 2 |
| Roll 2 Speed, meter/min | 18 | 18 |
| Draw Ratio | 9 to 1 | 9 to 1 |

The tape was coated with a microcrystalline wax, W445, as described in Example 1, where the coated tape was designated as Run 1a.

The compression and recovery expansion of the tapes was measured as described in Example 1. The percent compression and percent recovery of each of the tapes were measured, and the results are summarized on Table XXXI:

TABLE XXXI

Tape compression and recovery.

|  | Run 1a | Run 16 |
|---|---|---|
| Original Thickness, inches | 0.007 | 0.005 |
| Compression, % | 54 | 57 |
| Recovery, % | 52 | 76 |

The toughness of the tapes was conducted by measuring the cycles to failure for each of the tapes as described in Example 1. The results are summarized on Table XXXII:

TABLE XXXII

Cycles to Failure for Tapes

| Tape | Average |
|---|---|
| Run 1a | 10.3 |
| Run 16 | 2.0 |

Example 8

Dental tape spool rolls were formed in accordance with the coating and winding processes of the present invention and using the component sizes and/or type described below and summarized in Table XXXIII.

TABLE XXXIII

| Component | Type/Size |
|---|---|
| Pulley 82e | 14 Teeth |
| Pulley 82d | 17 Teeth |
| Pulley 82c | 19 Teeth |
| Pulley 82f | 14 Teeth |
| Pulley 82g | 16 Teeth |
| Pulley 82h | 20 Teeth |
| Traversing Cam | 11.5 inches, 6 turns end to end cam |
| Guide Traverse |  |

Ordering the above pulley sizes sequentially (e.g., 82e is connected to 82d which is connected 82c etc. as shown in FIG. 8) and determining the product of the ratios of the sizes of the sequentially ordered pulleys or Ratio A (as shown in I below)

$$\text{Ratio } A = P_1/P_2 \times P_3/P_4 \times P_{Z-1}/P_Z \qquad \text{I}$$

Where $P_1$ to $P_Z$ are the sizes of the pulleys sequentially ordered from spool 72 and to the traverse barrel cam 86 of rewinding system 70, results in the following ratio:

Ratio $A$ = (Pulley 82e / Pulley 82d) ×

(Pulley 82c / Pulley 82f) × (Pulley 82g / Pulley 82h)

$= (14/17) \times (19/14) \times (16/20) = 0.8941$

A traverse barrel cam was selected to provide a traversing cam guide traverse of 11.5 inches end to end for every 6 revolutions of traverse barrel cam 86. This results in a cam advance equal to the following:

Cam Advance = Traversing Cam Guide

Traverse / 6 Revolutions of Traverse Barrel Cam $= 11.5/6 = 1.9166$ inches per Traverse Barrel Cam revolution Ratio A indicates that for each revolution of the spool 72, the traverse barrel cam travels 0.8941 of the spool revolution. This results in the following travel distance for the traversing cam guide 76 per revolution of spool 72:

Travel Distance of traversing cam guide per revolution of spool

= Cam Pulley Ratio × Cam Advance $= 0.8941 \times 1.9166 = 1.71$ inches per spool revolution The core diameter $d_s$ of spool 72 was measured to be 6.21 inches, therefore, the distance traveled by any point on the outer surface of the core of spool 72 after one revolution of spool 72 or circumference C can be calculated as follows:

Circumference $C = 6.21 \text{ inches} \times \pi = (6.21)3.1411 = 19.5$ inches

The helix angle θ (the angle formed by a strand of dental tape and plane rΦ of the spool which is perpendicular to the longitudinal axis z of the spool 72 as shown in FIG. 25) formed by dental tape 10 as it is initially wound around the core of spool 72 can then be calculated as follows:

Travel Distance of traversing cam guide per spool revolution/Circumference $C=1.71/19.5$ $1.71/19.5=0.0876=\sin^{-1} \theta$(Helix Angle)

Where Helix Angle $\theta'=5.03°$

As will be understood by the skilled artisan, as the spool 72 roll grows, the helix angle θ decreases. For example, as one inch of dental tape is wound onto the core of spool 72, helix angle decreases. This is exemplified as follows:

The diameter of spool after 1 adding one inch layer of tape=6.21 inches+2 inches (1 inch of added layer results in diameter increasing by 2 inches)=8.21 inches, hence:

Circumference of Spool with Tape = diameter of spool with tape $\times \pi$ $= (8.21)3.1411$ $= 25.7$ inches, hence Travel distance of traversing cam guide per spool revolution/Circumference of Spool and Tape=1.71/25.7 inches=0.066=$\sin^{-1} \theta'$(Helix Angle)

Where Helix Angle $\theta'=3.8°$

Therefore, as about an inch of material is wound around the spool, the helix angle chances by about 1° ($\theta-\theta'=5.03°-3.8°=1.5°$).

Using the above traverse barrel cam and pulley sizes, Rolls 1-7 (representative of spool 72 in FIG. 8) were formed and, then, Rolls 1-7 were subsequently used to form separate bobbins (representative bobbins formed on bobbin spool 90 in FIG. 8) The parameters of the formed rolls and coating and rewinding process are summarized in Tables XXXIV and XXXV.

TABLE XXXIV (Wax Coating Formulation)

| Ingredient | Amount (%) |
|---|---|
| Microcrystaline Wax[1] | 82% |
| Flavor | 17% |
| Sodium Saccharin | 1% |

[1]Multiwax-W445, supplied by Crompton Corp. Petrolia, Pa

TABLE XXXV

| Process Parameters | Roll 1 | Roll 2 | Roll 3 | Roll 4 | Roll 5 | Roll 6 | Roll 7 |
|---|---|---|---|---|---|---|---|
| Line Speed (feet per min.) | 1600 | 1600 | 1600 | 1600 | 1600 | 1600 | 1600 |
| Tape Tension prior to rewinding on rolls (grams-force) | 190 | 190 | 200 | 205 | 205 | 200 | 210 |
| Tank Temp ° F. | 200 | 200 | 200 | 200 | 200 | 200 | 200 |
| Die Temp ° F. | 200 | 200 | 200 | 200 | 200 | 200 | 200 |
| Tape (yarn) Start Wt (grams). | 3738 | 2907 | 3994 | 2998 | 2257 | 3804 | 2977 |
| Tape (yarn) Finish Wt (grams). | 2907 | 2079 | 2998 | 2257 | 1364 | 2977 | 2131 |
| Tape (yarn) Wt. (grams) | 831 | 828 | 996 | 741 | 893 | 827 | 846 |
| Coated Tape and Core (grams) | 2578 | 2661 | 2704 | 2637 | 2654 | 2704 | 2630 |
| Core Tare (grams) | 1398 | 1462 | 1309 | 1367 | 1357 | 1474 | 1370 |
| Coated Tape Wt. (grams) | 1180 | 1199 | 1395 | 1270 | 1297 | 1230 | 1260 |
| Wax Added[1] (grams) | 349 | 371 | 409 | 329 | 406 | 403 | 414 |
| Wax Add-on %[2] | 29.5 | 31.3 | 306 | 30.7 | 31.2 | 32.7 | 32.8 |
| Wt. Roll[3] (lbs.)t | 2.60 | 2.65 | 2.94 | 2.35 | 2.86 | 2.71 | 2.77 |

[1]Wax Added = Tape Wt. − Coated Tape Wt.
[2]Wax Add-on % = (Waxed Added/Coated Tape Wt.) (100)
[3]Wt. Roll = Coated Tape Wt./454 grams/lb.

The bobbins produced on bobbin spools of width 10.3 mm and percent of bobbins rejected as exhibiting unsatisfactory telescoping are summarized in Table XXXVI.

TABLE XXXVI

| | # Bobbin Produced | | | | | | |
|---|---|---|---|---|---|---|---|
| | 236 | 240 | 261 | 213 | 259 | 296 | 251 |
| # Rejects[1] | 0 | 0 | 0 | 8 | 1 | 0 | 0 |

[1]Rejected bobbins rolls are bobbin rolls in which the width of the wound tape on bobbin exceeded the bobbin dispenser width of 11.2 mm.

Total Bobbins Produced=1711
Total Rejects=9
% Rejects=0.5%

Example 9

The effectiveness of the ribbed dental tape of the present invention is demonstrated in the following clinical tests.

Two clinical studies (Trial 1 and Trial 2) were performed, employing a single-center, three-way crossover design. The observers were blinded and the comparative groups were coded.

The subjects participated in 3 treatment visits (at least 24-hour between each crossover period). Subjects refrained from oral hygiene procedures for 18-24 hours prior to each visit. During the treatment visit, pre-flossing Proximal/Marginal Plaque Index (PMI) assessments were made on each subject prior to surrogate flossing by a trained dental hygienist. The surrogate flossing of the subjects was followed by a post-flossing PMI assessment. The flosses tested included a dental tape prepared in accordance with the conditions of and having the properties of Examples 1-8 of the present invention (Tape A); Crest® Glide® Mint dental floss (Floss A); and Oral-B SATINfloss® dental floss (Floss B).

Supragingival plaque levels on the facial and lingual surfaces of the mandibular and maxillary lateral and central incisors were assessed using the Proximal/Marginal Plaque Index (PMI) following disclosing. The facial and lingual surfaces were divided into three unequal segments: distal proximal, marginal and mesial proximal; however, the marginal surfaces were not scored. Effectiveness was determined by change from baseline in mean PMI. Plaque was scored using the following criteria:

0=No plaque.
1=Separate flecks of plaque covering less than ⅓ of the area.
2=Discrete areas or bands of plaque covering less than ⅓ of the area.
3=Plaque covering ⅓ of the area.
4=Plaque covering more than ⅓ but less than ⅔ of the area.
5=Plaque covering ⅔ or more of the area The results are summarized in Tables XXXVII and XXXVIII

TABLE XXXVII

Trial 1

|  | Tape A | Floss A | Floss B |
| --- | --- | --- | --- |
| No. of Participants per testing group | 39 | 40 | 37 |
| Pre-Flossing PMI Mean | 2.885 | 2.955 | 2.928 |
| Post-Flossing PMI Mean | 1.681 | 2.385 | 2.296 |
| Change from Pre-Flossing | −1.2176 (42.20%) | −0.5601 (18.95%) | −0.6397 (21.85%) |
| % Difference vs. Floss A | 117.4% |  |  |
| % Difference vs. Floss B | 90.3% |  |  |

TABLE XXXVIII

Trial 2

|  | Tape A | Floss A | Floss B |
| --- | --- | --- | --- |
| N | 30 | 30 | 30 |
| Pre-Flossing PMI Mean | 2.499 | 2.350 | 2.517 |
| Post-Flossing PMI Mean | 1.180 | 1.674 | 1.764 |
| Change from Pre-Flossing | −1.3099 (45.42%) | −0.6974 (29.68%) | −0.7406 (29.42%) |
| % Difference vs. Floss A | 87.8% |  |  |
| % Difference vs. Floss B | 76.9% |  |  |

We claim:

1. A bobbin of elastomeric tape suitable for movable connection within a housing of a dental tape dispenser, the bobbin comprising:
   a. a bobbin spool core having a width; and
   b. an elastomeric dental tape wound onto the bobbin spool core such that it forms a wound tape width, the elastomeric dental tape comprising:
      i. a core body comprising a first cleaning surface and a second cleaning surface opposite said first cleaning surface, said core body having an aspect ratio of greater than about 10:1; and
      ii. a plurality of ribs disposed along at least one of said first and second cleaning surfaces, wherein the ratio of the width of said dental tape to the thickness of said dental tape is from about 3:1 to about 25:1,
   wherein the wound tape width formed by the elastomeric dental tape exceeds the bobbin spool core width by no more than 10 percent, whereby the wound tape width does not telescope so as to interfere with movable connection of the bobbin within the housing of the dental tape dispenser.

2. The bobbin of claim 1, wherein the wound width formed by the elastomeric dental tape exceeds the width of the bobbin spool core by no more than 7.5 percent.

3. The bobbin of claim 2, wherein the wound width formed by the elastomeric dental tape exceeds the width of the bobbin spool core by no more than 5 percent by no more than 5 percent of the width of the spool.

4. The bobbin of claim 1, wherein the aspect ratio of the bobbin spool core is greater than about 2:1.

5. The bobbin of claim 4, wherein the aspect ratio of the bobbin spool core is greater than about 3:1.

6. The bobbin of claim 1, wherein the elastomeric dental tape further comprises uniform or substantially uniform coating on the first and second surfaces.

7. A dental tape dispenser comprising
   A. a housing;
   B. a bobbin movably connected within the housing, the bobbin comprising:
      i. a bobbin spool core having a width; and
      ii an elastomeric dental tape wound onto the spool such that it forms a wound tape width, the elastomeric dental tape comprising:
         a. a core body comprising a first cleaning surface and a second cleaning surface opposite said first cleaning surface, said core body having an aspect ratio of greater than about 10:1; and
         b. a plurality of ribs disposed along at least one of said first and second cleaning surfaces,
      wherein the ratio of the width of said dental tape to the thickness of said dental tape is from about 3:1 to about 25:1, wherein the wound width formed by the elastomeric tape exceeds width of the bobbin spool core by no more than 10 percent, whereby the wound tape width does not telescope so as to interfere with movable connection of the bobbin within the housing of the dental tape dispenser.

8. The dental tape dispenser of claim 7, wherein the elastomeric dental tape further comprises uniform or substantially uniform coating on the first and second surfaces.

* * * * *